(12) United States Patent
Felton et al.

(10) Patent No.: US 11,478,354 B2
(45) Date of Patent: Oct. 25, 2022

(54) PENILE PROSTHESIS ANCHORING SYSTEM

(71) Applicant: Boston Scientific Scimed, Inc., Maple Grove, MN (US)

(72) Inventors: Jessica Elizabeth Felton, Minneapolis, MN (US); John Anders Bostrom, Minneapolis, MN (US); Julie Andreen, Huntersville, NC (US); Bernard Andre Wasscher, Mound, MN (US); Grady Jensen, Chanhassen, MN (US); Michael Wasson, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 59 days.

(21) Appl. No.: 16/947,475

(22) Filed: Aug. 3, 2020

(65) Prior Publication Data
US 2021/0038391 A1 Feb. 11, 2021

Related U.S. Application Data

(60) Provisional application No. 62/884,810, filed on Aug. 9, 2019.

(51) Int. Cl.
*A61F 2/26* (2006.01)

(52) U.S. Cl.
CPC .......... *A61F 2/26* (2013.01); *A61F 2220/005* (2013.01); *A61F 2220/0016* (2013.01); *A61F 2220/0083* (2013.01)

(58) Field of Classification Search
CPC ................ A61F 2/26; A61F 2220/0016; A61F 2220/005; A61F 2220/0083
See application file for complete search history.

(56) References Cited

U.S. PATENT DOCUMENTS

| | | |
|---|---|---|
| 2014/0343612 A1 | 11/2014 | Rezach et al. |
| 2018/0098854 A1 | 4/2018 | Allen et al. |
| 2019/0099272 A1 | 4/2019 | Newman et al. |
| 2020/0129295 A1 | 4/2020 | Kansas et al. |

OTHER PUBLICATIONS

International Search Report and Written Opinion for PCT Application No. PCT/US2020/070355, dated Nov. 12, 2020, 12 pages.

*Primary Examiner* — John P Lacyk
(74) *Attorney, Agent, or Firm* — Brake Hughes Bellermann LLP

(57) ABSTRACT

An implantable device for penile construction can comprise an anchor plate and at least one attachment member. The anchor plate can be configured to engage with a first portion of a pelvic bone of a patient. The anchor plate can comprise a prosthesis attachment interface configured to be coupled to a penile prosthesis, and at least one attachment member configured to attach to the anchor plate. The at least one attachment member can be configured to engage with a second portion of the pelvic bone of the patient. The engagement of the anchor plate with the first portion of the pelvic bone and the engagement of the attachment member with the second portion of the pelvic bone can couple the pelvic bone between the anchor plate and the at least one attachment member.

10 Claims, 19 Drawing Sheets

PENILE PROSTHESIS ANCHORING SYSTEM

CROSS-REFERENCE TO RELATED APPLICATION

This application claims priority to U.S. Provisional Patent Application No. 62/884,810, filed on Aug. 9, 2019, entitled "PENILE PROSTHESIS ANCHORING SYSTEM", which is incorporated by reference herein in its entirety.

TECHNICAL FIELD

This description relates generally to attachment plates and implants for penile construction.

BACKGROUND

In some examples, penile prostheses for erectile dysfunction have been used off-label in penile construction or reconstruction cases such as female to male transgender, and natal males with penile reconstruction (e.g., congenital disorders, amputation (penile cancer), trauma, etc.). For example, a patient undergoes a phalloplasty procedure (e.g., single stage or multiple stages) in which a neophallus is surgically constructed from tissue grafts taken from other parts of the body. The phalloplasty procedure may be considered highly invasive with relatively high infection risks, and a patient may be open on the operating table for an extended period of time (e.g., 8+ hours). Since the neophallus is made of skin and does not contain the erectile tissues of a biological penis, the neophallus does not have the capability to achieve an erection.

A penile prosthesis may be implanted after the phalloplasty procedure. In some examples, the penile prosthesis may be a transgender specific device or a penile prosthesis used for erectile dysfunction in natal males. However, there may be difficulties associated with how the penile prosthesis is attached to the pelvic bone. In natal males, the proximal ends of the corpora cavernosa tunnel deep into the pelvic bone, and, in some examples, they provide the cavity in which the two cylinders of the penile prosthesis are disposed, as well as a way to prevent migration or crossover of the cylinders. In the natal males undergoing penile reconstruction due to amputation, the proximal corpora cavernosa may still be intact and may serve to anchor the proximal ends of the penile prosthesis dual cylinders. However, in transgender, natal males with birth defects, and/or severe trauma cases, these features of the proximal corpora cavernosa may not be present in the same manner, and there may be difficulties with anchoring these devices to the pelvic bone.

SUMMARY

An implantable device for penile construction can comprise an anchor plate and at least one attachment member. The anchor plate can be configured to engage with a first portion of a pelvic bone of a patient. The anchor plate can comprise a prosthesis attachment interface configured to be coupled to a penile prosthesis, and at least one attachment member configured to attach to the anchor plate. The at least one attachment member can be configured to engage with a second portion of the pelvic bone of the patient. The engagement of the anchor plate with the first portion of the pelvic bone and the engagement of the attachment member with the second portion of the pelvic bone can couple the pelvic bone between the anchor plate and the at least one attachment member.

An implantable device for penile construction can comprise an anchor plate and at least one clamp. The anchor plate can be configured to engage with a first portion of a pelvic bone of a patient. The anchor plate can comprise a prosthesis attachment interface configured to be coupled to a penile prosthesis. The prosthesis attachment interface can comprise an elastic material. The at least one clamp can be rotatably attached to the anchor plate. The at least one clamp can be configured to engage with a second portion of the pelvic bone of the patient. The engagement of the anchor plate with the first portion of the pelvic bone and the engagement of the at least one clamp with the second portion of the pelvic bone can friction-fit the pelvic bone between the anchor plate and the at least one clamp.

An implantable device for penile construction can comprise an anchor plate and at least one strap. The anchor plate can be configured to engage with a first portion of a pelvic bone of a patient. The anchor plate can comprise a prosthesis attachment interface configured to be coupled to a penile prosthesis. The prosthesis attachment interface can comprise an elastic material. The at least one strap can be attached to the anchor plate. The at least one strap can be configured to engage with a second portion of the pelvic bone of the patient. The engagement of the anchor plate with the first portion of the pelvic bone and the engagement of the at least one strap with the second portion of the pelvic bone can friction-fit the pelvic bone between the anchor plate and the at least one strap.

The details of one or more implementations are set forth in the accompanying drawings and the description below. Other features will be apparent from the description and drawings, and from the claims.

DETAILED DESCRIPTION

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the present disclosure.

The terms "a" or "an," as used herein, are defined as one or more than one. The terms "including" and/or "having", as used herein, are defined as comprising (i.e., open transition). The term "coupled," as used herein, is defined as connected, although not necessarily directly and mechanically.

In general, the embodiments are directed to bodily implants. The term patient or user may hereafter be used for a person who benefits from the medical device or the methods disclosed in the present disclosure. For example, the patient can be a person whose body is implanted with the medical device or the method disclosed for operating the medical device by the present disclosure.

Figure 1:
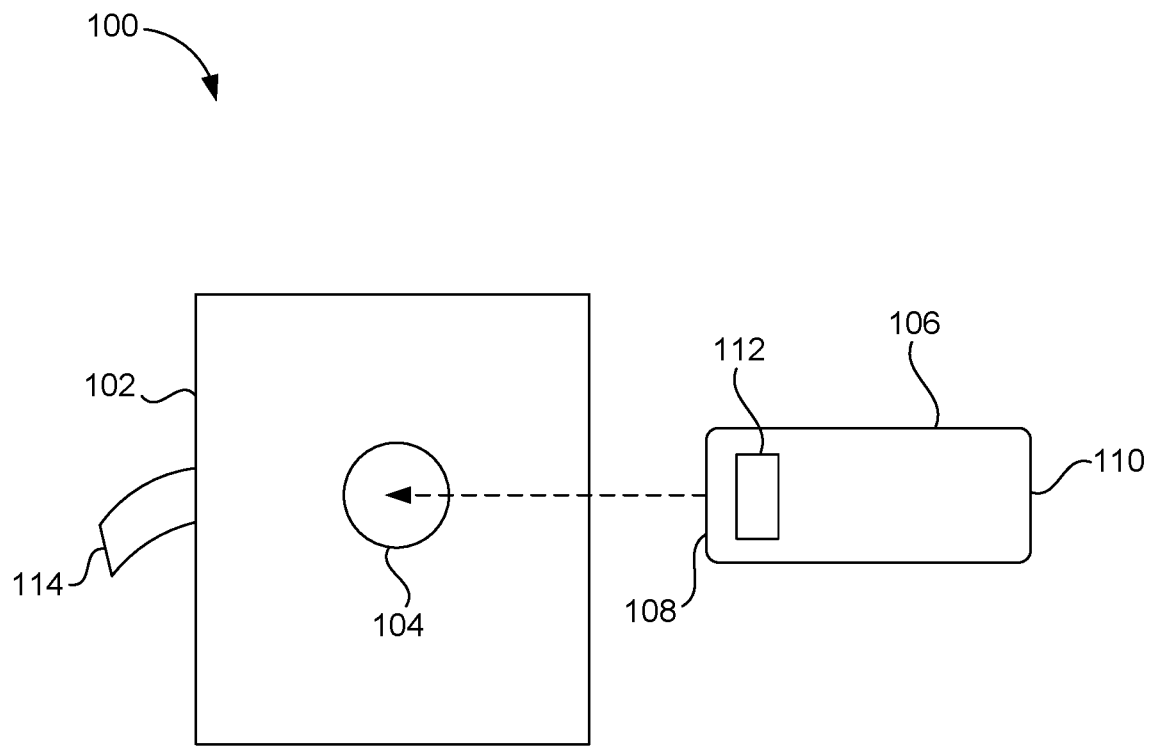
FIG. 1 illustrates an implantable device having an anchor plate for penile construction according to an aspect.

FIG. 1 illustrates an implantable device 100 for penile construction according to an aspect. The implantable device 100 may be used for female to male (FTM) or natal males undergoing penile construction (or reconstruction). The implantable device 100 includes an anchor plate 102 configured to be coupled to a pelvic bone of a patient. In some examples, the anchor plate 102 is permanently coupled to the pelvic bone. In some examples, the anchor plate 102 is temporarily coupled to the pelvic bone. In some examples, the anchor plate 102 is coupled to the pelvic bone using one or more attachment members such as clamps, straps, or mesh. Attachment members such as clamps, straps, or mesh can allow for later revisions without damaging the pelvic bone.

In some examples, the anchor plate 102 is configured to engage with a first portion of the pelvic bone. In some examples, the implantable device 100 can include at least one attachment member 114. In some examples, the at least one attachment member 114 is configured to attach to the anchor plate 102. In some examples, the at least one attachment member 112 is rotatably attached to the anchor plate 102. In some examples, the anchor plate 102 is attached, fastened, coupled, and/or secured to the pelvic bone using the at least one attachment member 114. The at least one attachment member 114 can be configured to engage with a second portion of the pelvic bone of the patient. The engagement of the anchor plate 102 with the first portion of the pelvic bone and the engagement of the at least one attachment member 114 with the second portion of the pelvic bone can couple and/or friction-fit the pelvic bone between the anchor plate 102 and the at least one attachment member 114. The attachment member 114 can include, for example, at least one clamp, at least one strap, and/or at least one mesh. In some examples, the anchor plate 102 includes tissue ingrowth materials (e.g., hydroxyapatite) to allow bone to grow into the anchor plate 102 for attachment of the anchor plate 102.

The anchor plate 102 may be attached bilaterally or unilaterally to the pelvic bone. The anchor plate 102 may encompass a wide variety of shapes to accommodate patient pelvic anatomy and penile prosthesis attachment. The anchor plate 102 may include unique "male" and "female" versions to account for differences in pelvic anatomy and desired take-off angle and positioning of the penile prosthesis from the pelvis.

In some examples, the anchor plate 102 may include materials that are both stiff and flexible. In some examples, the anchor plate 102 defines one or more flexible areas. Each flexible area may include a material that is more flexible than the material(s) between (or surrounding) a respective flexible area. In some examples, a flexible area can be defined at a center region of the anchor plate 102, where the flexible area may operate as an elastomeric flex point. In some examples, a flexible area is defined on one or more sides of an attachment interface 104. The prosthetic attachment interface 104 can include an elastic material, defining the flexible area, to attach to the anchor plate 102 and to the penile prosthesis and/or elongated member 106. The flexible area(s) may allow for flexing at the pubic symphysis.

In some examples, the area surrounding the attachment interface 104 (e.g., where the anchor plate 102 interfaces with the elongate member 106) can include a softer material (than other areas of the anchor plate 102) in order to dampen the transfer of forces between the anchor plate 102 and the elongated member 106 during use. In some examples, the anchor plate 102 can include one or more securement interfaces for securing the one or more attachment members to the anchor plate 102. In some examples, the anchor plate 102 includes reinforcement fibers that may be used in specific areas of the anchor plate 102. In some examples, the anchor plate 102 includes a textile or other porous substrate that may be used as the flexible material or to promote tissue ingrowth in specific areas. In some examples, the anchor plate 102 may include a coated or dipped elastomeric polymer to control the tissue ingrowth in certain areas and allow for expansion of the anchor plate 102. In some examples, the anchor plate 102 includes cadaveric bone, animal biologic tissues, and materials known for tissue ingrowth properties, which may be used to help fuse the anchor plate 102 to the patient such as porous, hydroxyapatite-type of material for bone/tissue ingrowth.

The anchor plate 102 can include the prosthesis attachment interface 104 configured to be coupled to an elongated member 106 of a penile prosthesis. In some examples, the prosthesis attachment interface 104 can be configured to be attached to a penile prosthesis. The penile prosthesis can have features of the elongated member 106. In some examples, the elongated member 106 is configured to be inserted into a neophallus, e.g., a newly constructed shaft of skin in the shape of a penis, where the neophallus is formed from tissue donated from a body part (e.g., thigh, forearm) of the patient. In some examples, the penile prosthesis is a neophallus implant. In some examples, the penile prosthesis is a penile prosthesis originally designed for erectile dysfunction. In some examples, the penile prosthesis is an adjustable member configured to increase in length over time to assist with the creation of a neophallus. In some examples, the penile prosthesis is a penile sheath that defines one or more lumens (or a solid core), where the penile sheath is configured to accommodate the neourethra within the neophallus. In some examples, the penile prosthesis is a hydraulic penile prosthesis in which the elongated member 106 is an inflation member (e.g., a single cylinder) that receives fluid from a fluid reservoir via a pump assembly. In some examples, the penile prosthesis is a malleable penile prosthesis in which the elongated member 106 is malleable.

The elongated member 106 includes a proximal end portion 108 and a distal end portion 110. In some examples, the proximal end portion 108 is a rear tip of a penile implant. The proximal end portion 108 defines an attachment interface 112 that is configured to interact with the attachment interface 104 of the anchor plate 102 (after the anchor plate 102 is attached to the pelvic bone) in order to couple the elongated member 106 to the anchor plate 102. In some examples, the coupling of the attachment interface 104 with the attachment interface 112 may allow for orbital movement of the elongated member 106. In some examples, the attachment interface 104 of the anchor plate 102 is coupled to the attachment interface 112 of the elongated member 106 using a snap-fit (e.g., the proximal end portion 108 is snap-fitted into the anchor plate 102). In some examples, the attachment interface 104 is coupled to the attachment interface 112 using a friction fit. In some examples, the attachment interface 104 and the attachment interface 112 may define a ball and socket connection, a tongue and groove connection, or mortise and tenon mating connection.

Figure 2A:
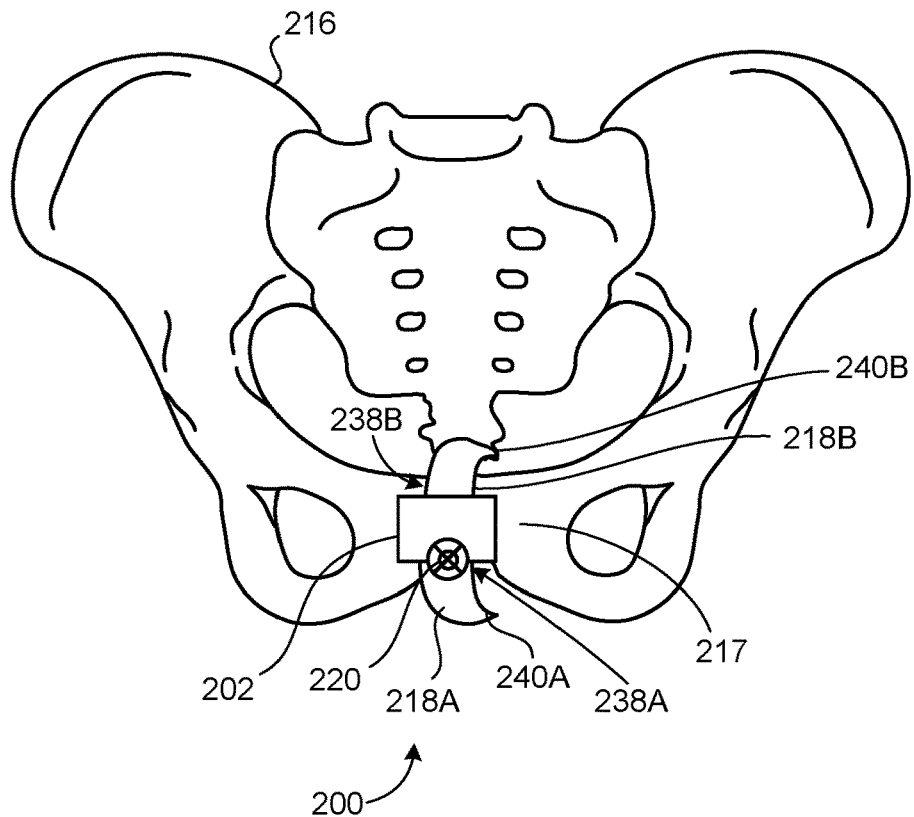
FIG. 2A illustrates a pelvic bone and an implantable device for penile construction in an open position according to an aspect.

FIG. 2A illustrates a pelvic bone 216 and an implantable device 200 for penile construction in an open position according to an aspect. The implantable device 200 can include any combination of features described above with reference to the implantable device 100.

The implantable device 200 can include an anchor plate 202. The anchor plate 202 can include any combination of features described above with reference to the anchor plate 102. The anchor plate 202 can engage with a first portion of the pelvic bone 216, such as a front portion of a pubic symphysis 217 of the pelvic bone 216.

In some examples, the implantable device 200 includes two clamps 218A, 218B. The two clamps 218A, 218B are examples of the at least one attachment member 114 described above. The two clamps 218A, 218B can be attached to the anchor plate 202 at first end portions 238A, 238B of the clamps 218A, 218B. Second end portions 240A, 240B of the clamps 218A, 218B can be configured to engage the pelvic bone 216.

The two clamps 218A, 218B can be rotatably attached to the anchor plate 202. The rotatable attachment of the clamps 218A, 218B to the anchor plate 202 can enable the clamps 218A, 218B to extend around a portion of the pelvic bone 216, such as around the pubic symphysis 217. One or both of the clamps 218A, 218B can extend through a pelvic inlet defined by the pelvic bone 216.

In some examples, the implantable device 200 can include a tightening mechanism 220. The tightening mechanism 220 can reduce distances between the anchor plate 202 and the second end portions 240A, 240B of the clamps 218A, 218B. In some examples, the tightening mechanism 220 can include a rotating cam. The practitioner can tighten the clamps 218A, 218B by applying a disposable tool, or by hand, to the tightening mechanism. In some examples, the tightening mechanism 220 can include a rotating ratchet with at least one release button, and/or the tightening mechanism 220 can include at least one release button, to adjust the tension of the clamps 218A, 218B.

Figure 2B:
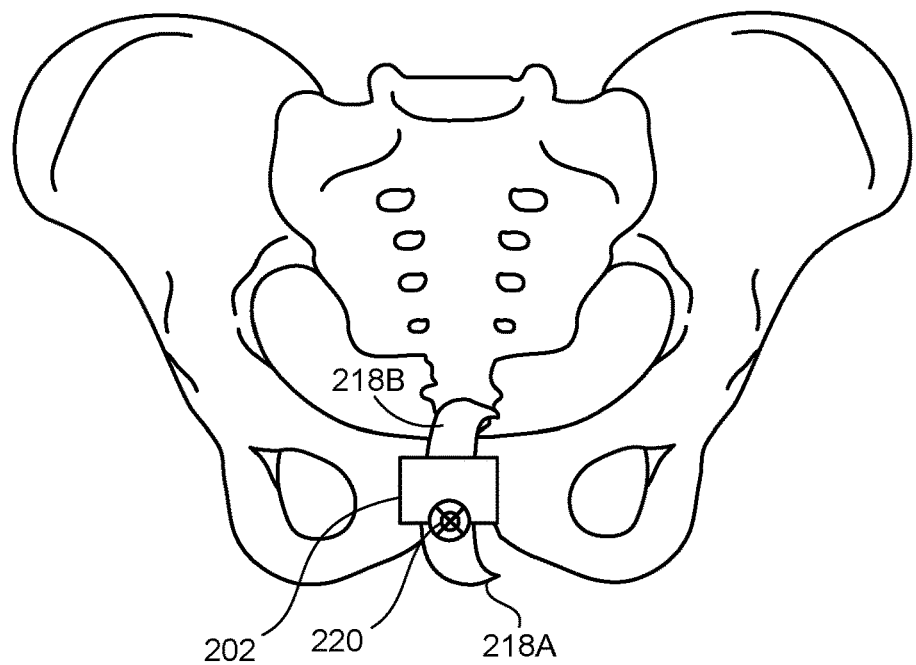
FIG. 2B illustrates a pelvic bone and an implantable device for penile construction in an open position according to an aspect.

FIG. 2B illustrates the pelvic bone 216 and the implantable device 200 for penile construction in an open position according to an aspect. In this example, a practitioner has engaged the tightening mechanism 220 to reduce the distance between the second end portions 240A, 240B (not shown in FIG. 2B) of the clamps 218A, 218B and the anchor plate 202. The reduction of the distance between the second end portions 240A, 240B and the anchor plate 202 causes the end portions 240A, 240B to engage second and third portions of the pubic symphysis 217 and/or pelvic bone 216 opposite from the first portion of the pubic symphysis 217 and/or pelvic bone 216 that is engaged by the anchor plate 202. The engagement of the first portion of the pubic symphysis 217 and/or pelvic bone 216 by the anchor plate 202 and the engagement of the second and third portions of the pubic symphysis 217 and/or pelvic bone 216 by the clamps 218A, 218B secures the implantable device 200 to the pubic symphysis 217 and/or pelvic bone 216.

Figure 3A:
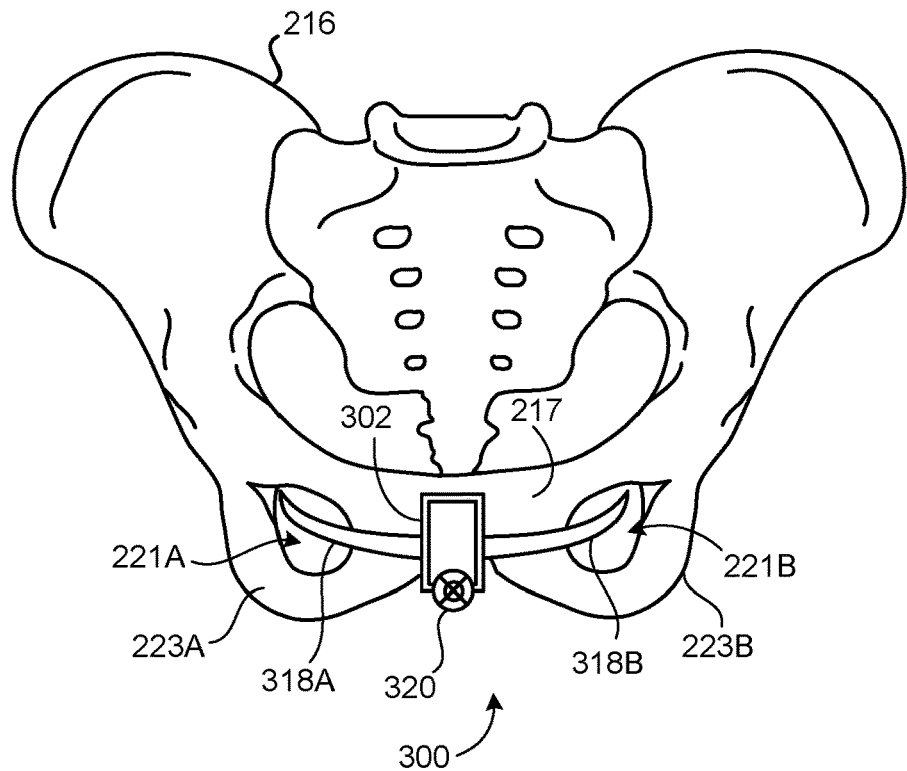
FIG. 3A illustrates a pelvic bone and an implantable device for penile construction in an open position according to an aspect.

FIG. 3A illustrates the pelvic bone 216 and an implantable device 300 for penile construction in an open position according to an aspect. The implantable device 300 can include any combination of features of the implantable devices 100, 200 described above.

In this example, the implantable device 300 can include two clamps 318A, 318B rotatably attached to an anchor plate 302. The anchor plate 302 and clamps 318A, 318B can include any combination of features described above with respect to the anchor plate 102, 202 and clamps 218A, 218B and/or attachment member 114. In this example, the clamps 318A, 318B extend around the pubic symphysis 217 and through obdurator foramen 221A, 221B defined by ischia 223A, 223B.

The implantable device 300 can include a tightening mechanism 320. The tightening mechanism 320 can include any combination of features described above with reference to the tightening mechanism 220. The tightening mechanism 320 can reduce a distance between end portions of the clamps 318A, 318B and the anchor plate 302.

Figure 3B:
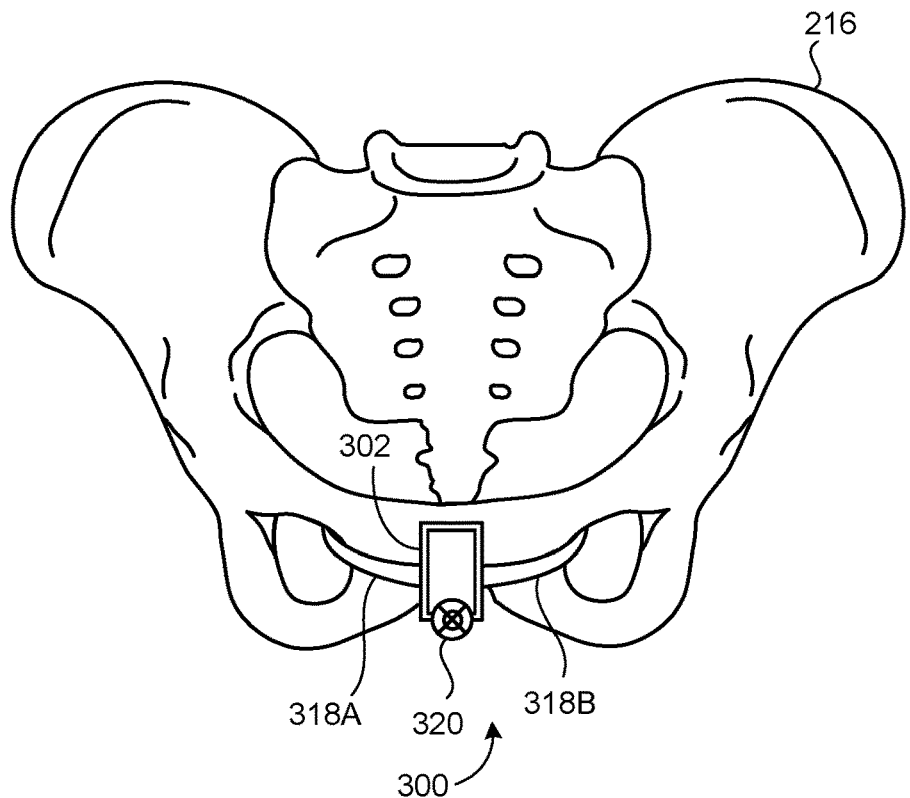
FIG. 3B illustrates a pelvic bone and an implantable device for penile construction in a closed position according to an aspect.

FIG. 3B illustrates the pelvic bone 216 and the implantable device 300 for penile construction in a closed position according to an aspect. In this example, the tightening mechanism 320 has reduced the distance between end portions of the clamps 318A, 318B and the anchor plate 302. The reduction of the distance between end portions of the clamps 318A, 318B and the anchor plate 302 causes the anchor plate 302 to engage a first portion of the pelvic bone 216 and the clamps 318A, 318B to engage second and third portions of the pelvic bone 216, securing the implantable device 300 to the pelvic bone 216.

Figure 4:
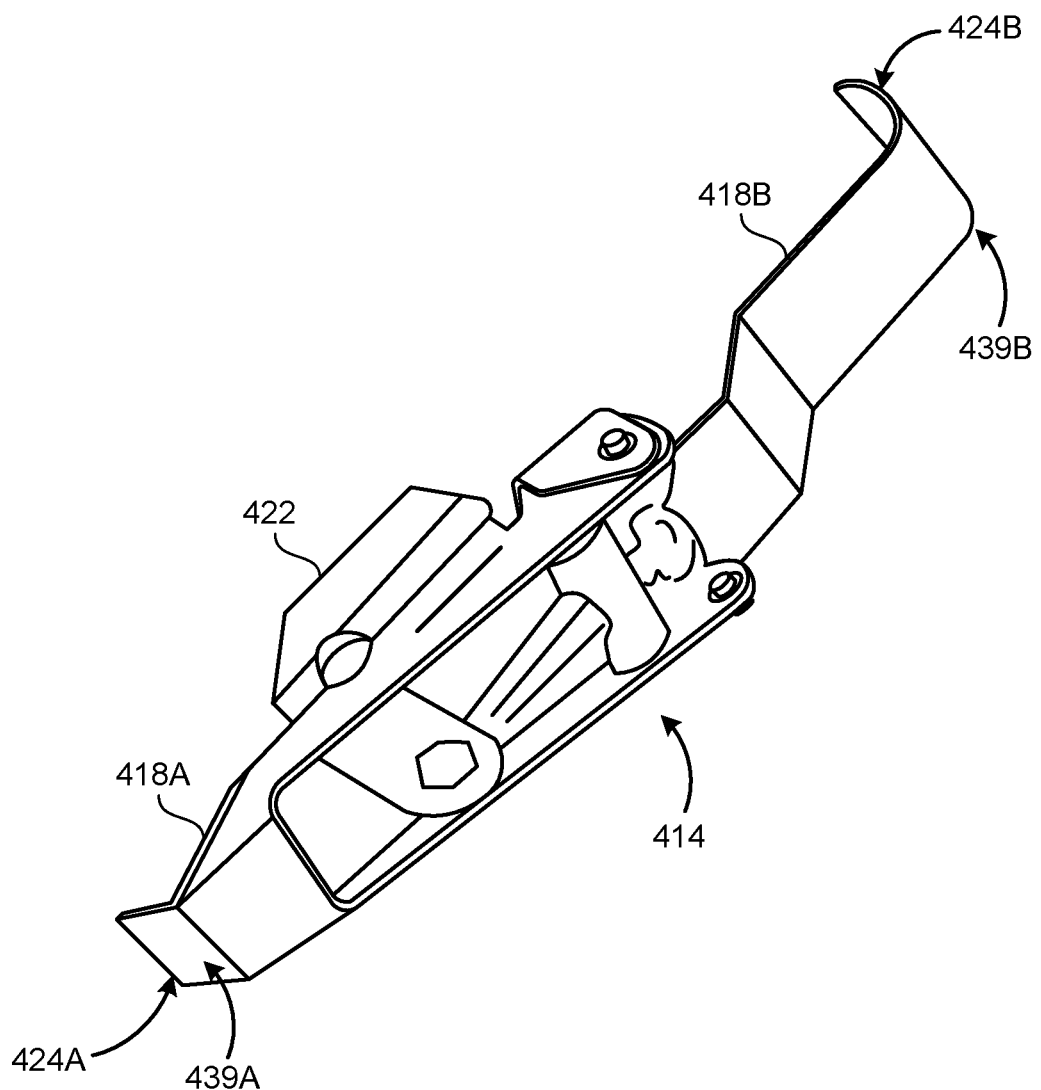
FIG. 4 illustrates an attachment member for securing, to a pelvic bone, an anchor plate of an implantable device for penile construction.

FIG. 4 illustrates an attachment member 414 for securing, to a pelvic bone, an anchor plate of an implantable device for penile construction. The attachment member 414 can be an example of the attachment member 114 described above with respect to FIG. 1. In some examples, the attachment member 414 can include a toggle-style clasp. The toggle-style clasp can enable the practitioner to secure the anchor plate (not shown in FIG. 4) to the pelvic bone 216, while also allowing for easy disassembly and/or detachment of the implantable device in the case of a revision surgery.

In some examples, the attachment member 414 can include a clamp attachment interface 422. The clamp attachment interface 422 can be shaped and/or configured to engage the anchor plate. In some examples, the clamp attachment interface 422 can comprise an anchor plate itself, and can attach directly to the pelvic bone 216 (not shown in FIG. 4)

In some examples, the attachment member 414 can include two clamps 418A, 418B. The clamps 418A, 418B can include any combination of features of the clamps 218A, 218B, 318A, 318B and/or attachment member(s) 114 described above. The clamps 418A, 418B can be rotatably attached to the clamp attachment interface 422. Each of the clamps 418A, 418B can include a hook 424A, 424B. The hook 424A, 424B can be disposed at an end portion 439A, 439B of the respective clamp 418A, 418B. The hooks 424A, 424B can loop toward the clamp attachment interface 422. The looping of the hooks 424A, 424B toward the clamp attachment interface 422 can enable the hooks 424A, 424B, when the clamp attachment interface 422 is engaged with the anchor plate and the anchor plate is engaged with the pelvic bone 216, to engage the pelvic bone 216, securing the implantable device to the pelvic bone 216.

Figure 5:
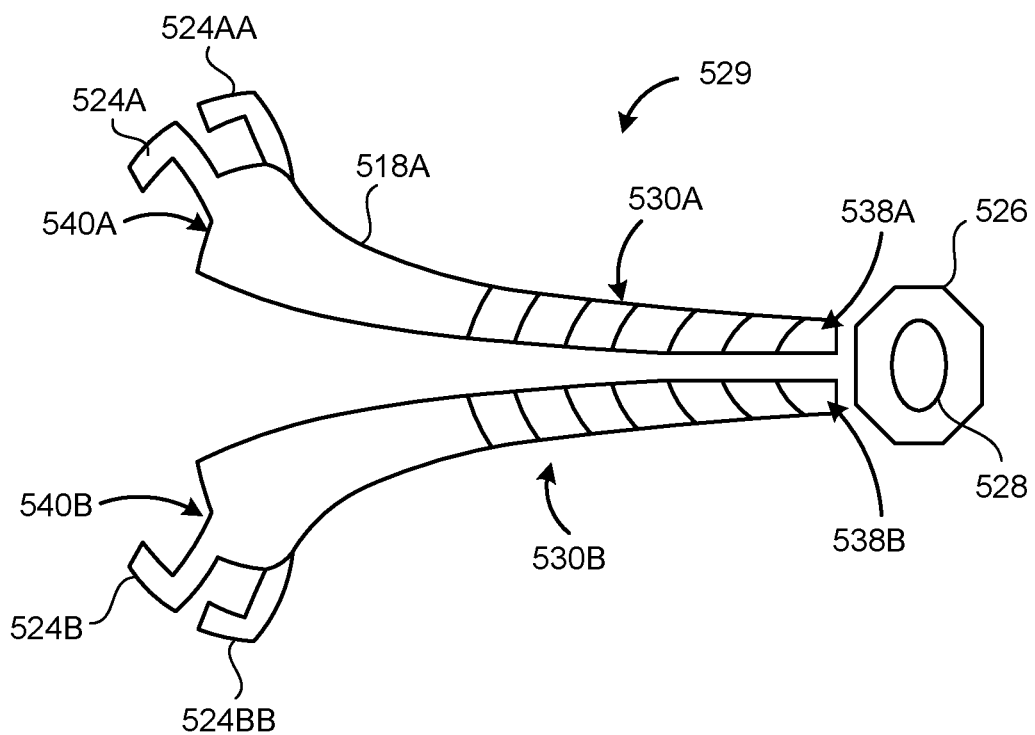
FIG. 5 illustrates a leaf spring for securing, to a pelvic bone, an anchor plate of an implantable device for penile construction.

FIG. 5 illustrates a leaf spring 529 for securing, to a pelvic bone 216, an anchor plate of an implantable device for penile construction. The leaf spring 529 can be an example of the attachment member 114 described above with respect to FIG. 1. The leaf spring 529 can include two clamps 518A, 518B and a nut 526 for tightening the clamps 518A, 518B toward each other. The clamps 518A, 518B can include any combination of features of the clamps 218A, 218B, 318A, 318B, 418A, 418B described above. The nut 526 can be an example of a tightening mechanism.

The clamps 518A, 518B can define clamp threads 530A, 530B. The clamp threads 530A, 530B can include alternating grooves and ridges. The clamp threads 530A, 530B in each of the clamps 518A, 518B can form a partial spiral pattern. When the clamps 518A, 518B are placed against each other, the clamp threads 530A, 530B of both of the clamps 518A, 518B can form a full spiral pattern.

The nut 526 can define nut threads 528 on an interior portion of the nut 526 that defines an aperture. The nut threads 528 can include alternating grooves and ridges in a spiral pattern. The spiral pattern of the nut threads 528 can match the spiral pattern formed by the clamp threads 530A, 530B when the clamps 518A, 518B are placed against each other.

When the clamps 518A, 518B are placed against each other, the nut 526 can be placed onto end portions 538A, 538B of the clamps 518A, 518B. The nut threads 528 can engage the clamp threads 530A, 530B. A practitioner can rotate the nut 526 to move the nut 526 away from the first end portions 538A, 538B toward second end portions 540A, 540B of the clamps 518A, 518B.

A width of a portion of the clamps 518A, 518B that defines the clamp threads 530A, 530B can increase as a function of a distance from a first end portion 538A, 538B of the clamps 518A, 518B. The rotation of the nut 526 to move the nut 526 away from the first end portions 538A, 538B and/or toward second end portions 540A, 540B of the clamps 518A, 518B can force the clamps 518A, 518B toward each other and/or tighten the clamps 518A, 518B.

Each of the clamps 518A, 518B can include one or more clamp hooks 524A, 524AA, 524B, 524BB. The clamp hooks 524A, 524AA, 524B, 524BB can extend from the second end portions 540A, 540B, opposite from the first end portions 538A, 538B onto which the nut 526 was placed. The tightening of the clamps 518A, 518B by rotating the nut 526 can create a compression force on the clamp hooks 524A, 524AA, 524B, 524BB toward the pelvic bone 216, securing the implantable device onto the pelvic bone 216.

Figure 6:
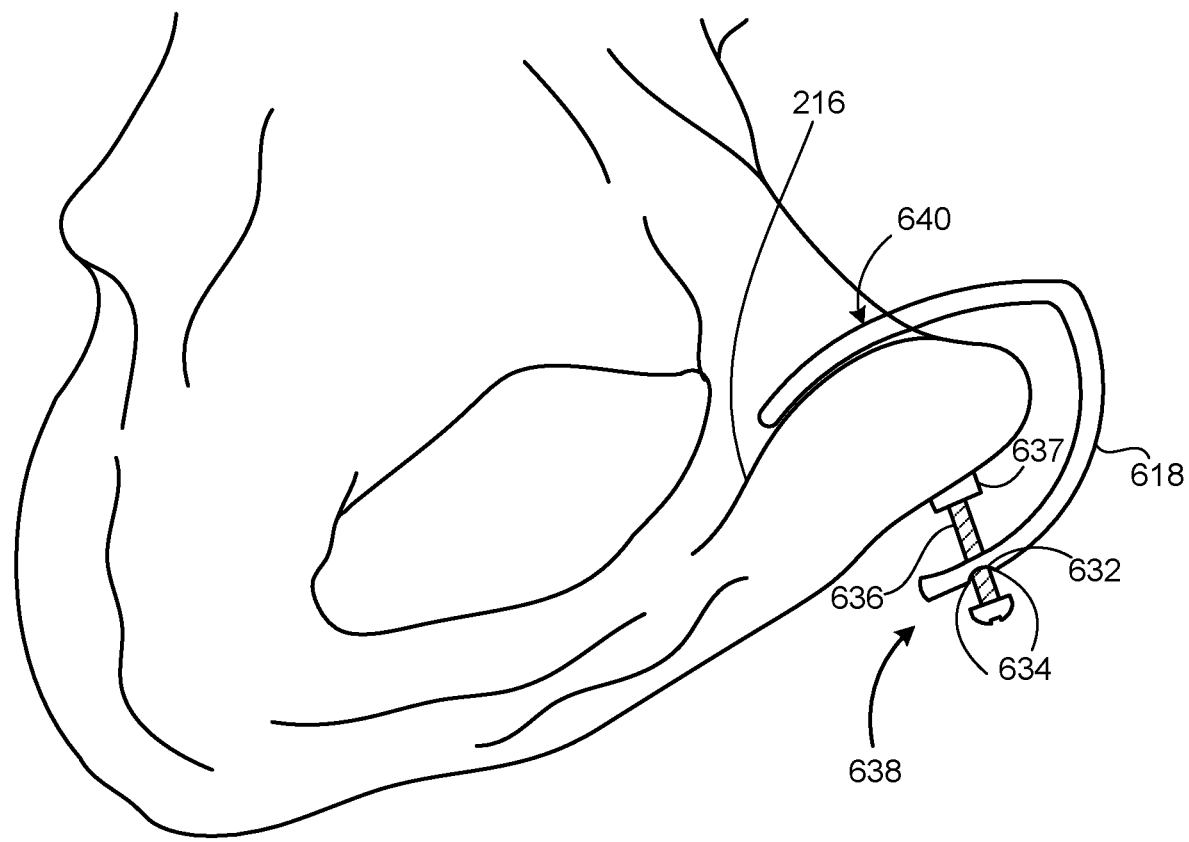
FIG. 6 illustrates a tightening mechanism, including a set screw, for securing, to a pelvic bone, an anchor plate of an implantable device for penile construction.

FIG. 6 illustrates a tightening mechanism, including a set screw 636, for securing, to a pelvic bone 216, an anchor plate of an implantable device for penile construction. In this example, a clamp 618 can define a clamp aperture 632. The clamp aperture 632 can define clamp aperture threads 634. The clamp aperture threads 634 can define alternating grooves and ridges in a spiral pattern. The clamp aperture 632 can be disposed near a first end portion 638 of the clamp 618. The clamp 618 can include any combination of features of the clamps 218A, 218B, 318A, 318B, 418A, 418B, 518A, 518B and/or attachment member(s) 114 described above.

A set screw 636 can extend through the clamp aperture 632. The set screw 636 can engage the clamp aperture threads 634 and press against the pelvic bone 216. Rotation of the set screw 636 can cause an end portion 637 of the set screw 636 to extend and/or move away from the first end portion 638 of the clamp 618. The movement of the end portion 637 of the set screw 636 away from the end portion 638 of the clamp 618, while the end portion of the set screw 636 is engaged with the pelvic bone 216, can cause the first end portion 638 of the clamp 618 to move away from the pelvic bone 216 and/or away from a second end portion 640 of the clamp 618. The movement of the first end portion 638 of the clamp 618 away from the second end portion 640 of the clamp 618 can cause a compression force on the second end portion 640 onto the pelvic bone 216 and/or a compression force on the end portion 637 of the set screw 636 onto the pelvic bone 216, securing the clamp 618 to the pelvic bone 216.

Figure 7:
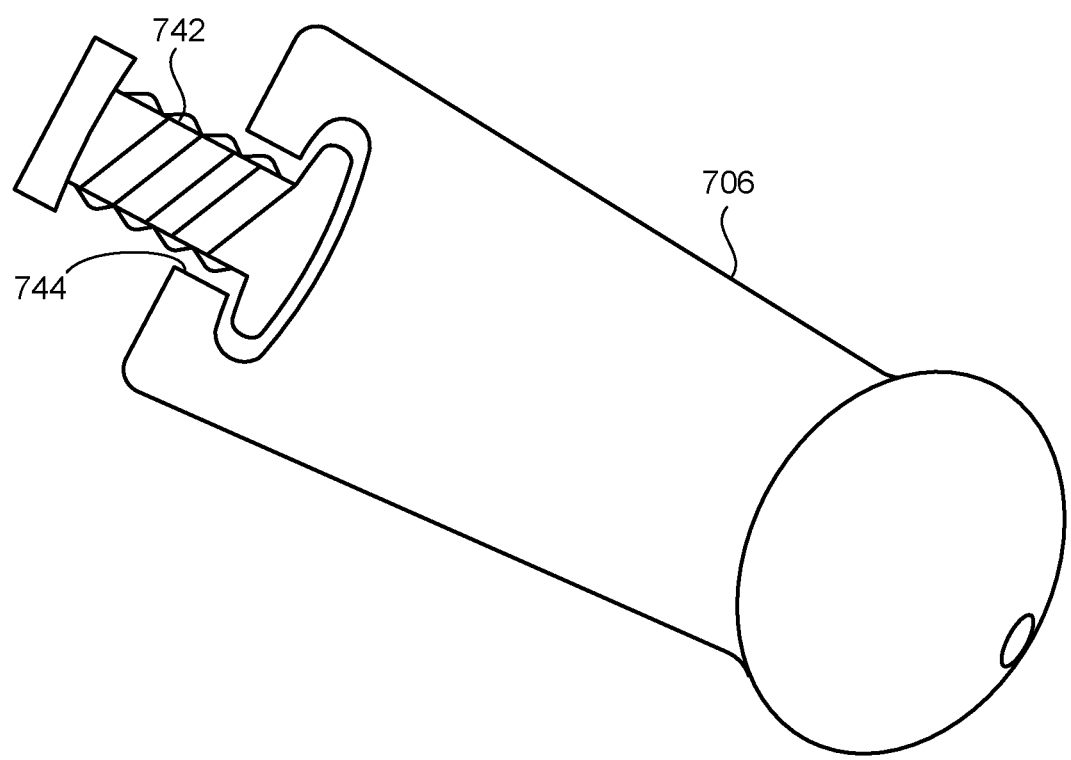
FIG. 7 illustrates a mechanism for attaching a penile prosthesis of an implantable device to an anchor plate of the implantable device.

FIG. 7 illustrates a mechanism for attaching a penile prosthesis 706 of an implantable device to an anchor plate of the implantable device. The penile prosthesis 706 can include any combination of the penile prosthesis and/or elongated member 106 described above.

In some examples, the penile prosthesis 706 can define a threaded aperture 744. The threaded aperture 744 can define alternating grooves and ridges in a spiral pattern.

The threaded aperture 744 of the penile prosthesis 706 can receive a threaded fastener 742. The threaded fastener 742 can define alternating grooves and ridges in a spiral pattern matching the threaded aperture 744 of the penile prosthesis 706. The threaded fastener 742 can be attached to the anchor plate, such as via the prosthesis attachment interface 104 in the example shown in FIG. 1. The reception of the threaded fastener 742 by the threaded aperture 744 can secure the penile prosthesis 706 to the anchor plate.

Figure 8:
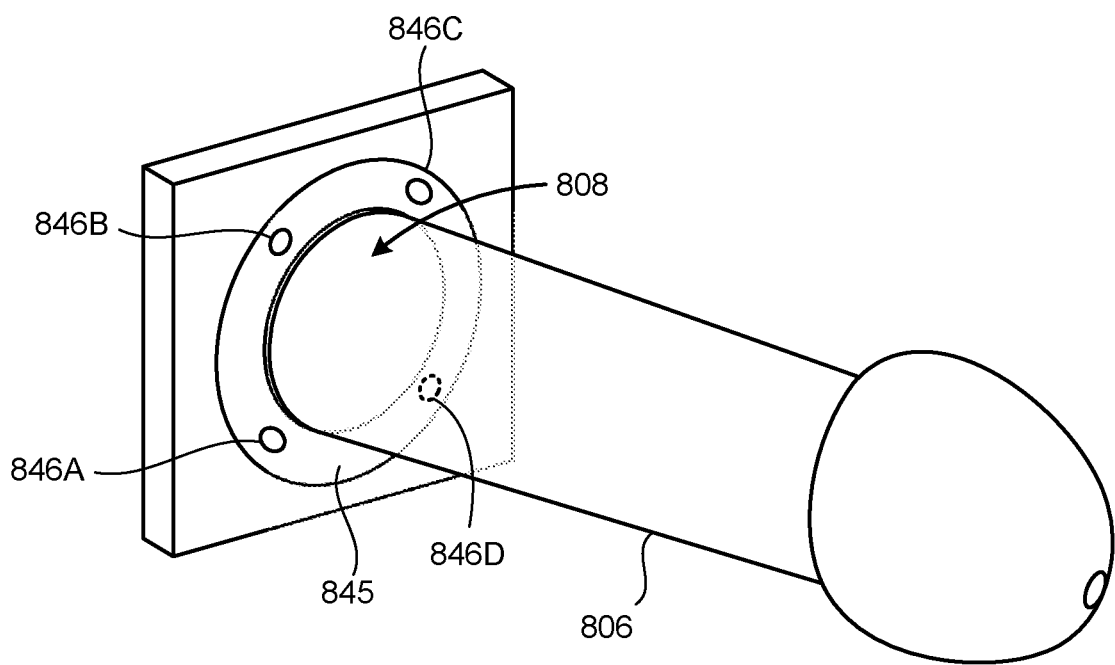
FIG. 8 illustrates a mechanism for attaching a penile prosthesis of an implantable device to an anchor plate of the implantable device.

FIG. 8 illustrates a mechanism for attaching a penile prosthesis 806 of an implantable device to an anchor plate 802 of an implantable device. The penile prosthesis 806 can have any combination of features of the penile prosthesis 706 and/or elongated member 106 described above. The anchor plate 802 can have any combination of features of the anchor plate 102, 202, 302 described above.

In some examples, a prosthesis base 845 can extend laterally from a prosthesis proximal end portion 808 of the penile prosthesis 806. The prosthesis base 845 can define one or more, or multiple, such as four, prosthesis attachment apertures 846A, 846B, 846C, 846D. The anchor plate 802 can also define one or more, or multiple, such as four, prosthesis anchor apertures. The prosthesis anchor apertures can be components of the prosthesis attachment interface 104 described above with respect to FIG. 1. The prosthesis anchor apertures can be aligned with the prosthesis attachment apertures 846A, 846B, 846C, 846D. The prosthesis anchor apertures can be threaded, and/or configured to receive threaded fasteners such as screws or bolts. A practitioner can secure the penile prosthesis 806 to the anchor plate 802 by inserting the threaded fasteners through the prosthesis attachment apertures 846A, 846B, 846C, 846D and into the prosthesis anchor apertures of the anchor plate 802.

Figure 9:
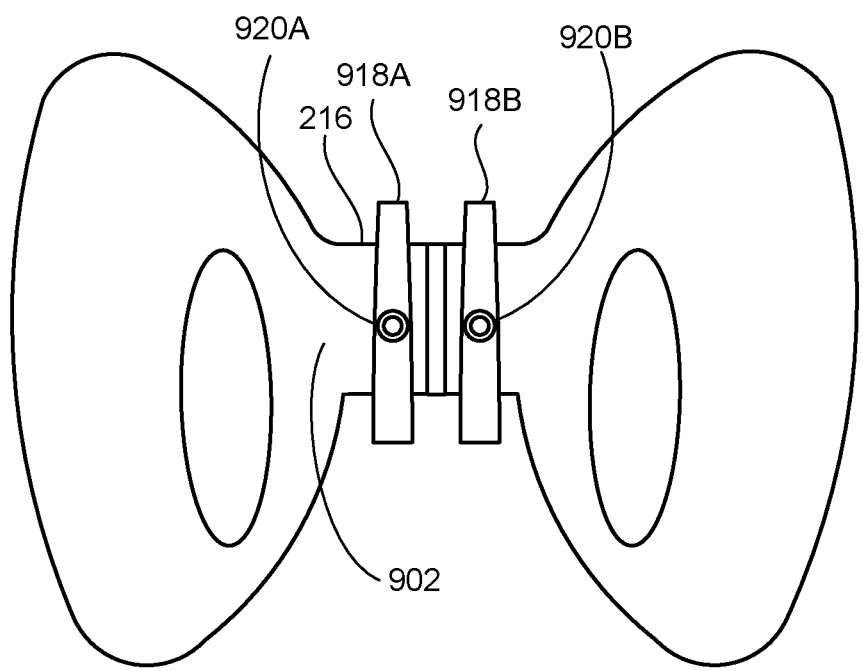
FIG. 9 illustrates a mechanism for securing an anchor plate of an implantable device to a pelvic bone.

FIG. 9 illustrates a mechanism for securing an anchor plate 902 of an implantable device to the pelvic bone 216. The anchor plate 902 can have any combination of features of the anchor plate 102, 202, 302, 802 described above. In this example, the implantable device includes two clamps 918A, 918B securing the anchor plate 902 to the pelvic bone 216 in a horizontal direction. The clamps 918A, 918B can include any combination of features of the clamps 218A, 218B, 318A, 318B, 418A, 418B, 518A, 518B, 618 and/or attachment member(s) 114 described above.

In some examples, first end portions of the clamps 918A, 918B can engage the anchor plate, and second end portions of the clamps 918A, 918B can engage the pelvic bone 216. Each of the clamps 918A, 918B can include a tightening mechanism 920A, 920B. The tightening mechanisms 920A, 920B can include any combination of features described above with respect to the tightening mechanism 220, 320, 420. In some examples, the tightening mechanisms 920A, 920B can include a set screw as described above with respect to FIG. 6. In some examples, the tightening mechanisms 920A, 920B can reduce a distance between the anchor plate 902, and/or first portion of the clamp 918A, 918B, and the second end portion of the clamp 918A, 918B, squeezing the pelvic bone 216 between the anchor plate 902 and/or first end portion of the clamp 918A, 918B and the second end portion of the clamp 918A, 918B.

In some examples, the tightening mechanisms 920A, 920B can include at least one tightening mechanism and/or two tightening mechanisms. The at least one tightening mechanism and/or two tightening mechanisms can adjust the two clamps 918A, 918B individually and/or independently, enabling a practitioner to create a secure fit of the anchor plate onto the pelvic bone. The at least one tightening mechanism and/or two tightening mechanisms 920A, 920B can, for example, reduce a distance between the second end portion of the first clamp 918A and the anchor plate 902 independently of a distance between the second end portion of the second clamp 918B and the anchor plate 902, and reduce the distance between the second end portion of the second clamp 918B and the anchor plate 902 independently of the distance between the second end portion of the first clamp 918A and the anchor plate 902.

Figure 10:
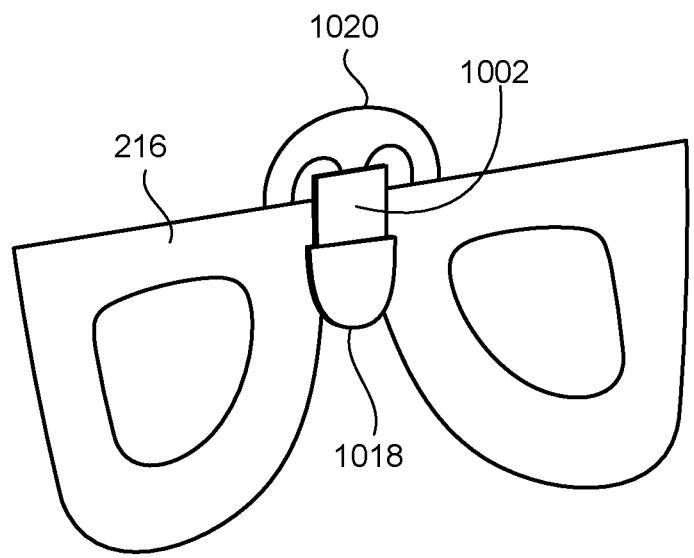
FIG. 10 illustrates a mechanism for securing an anchor plate of an implantable device to a pelvic bone.

FIG. 10 illustrates a mechanism for securing an anchor plate 1002 of an implantable device to a pelvic bone 216. In this example, a tightening mechanism 1020 tightens a clamp 1018, securing the anchor plate 1002 to the pelvic bone 216. The clamp 1018 can include any combination of features of the clamps 218A, 218B, 318A, 318B, 418A, 418B, 518A, 518B, 618, 918A, 918B and/or attachment member(s) 114 described above. The anchor plate 1002 can have any combination of features of the anchor plate 102, 202, 302, 802, 902 described above. The tightening mechanism 1020 can include any combination of features described above with respect to the tightening mechanism 220, 320, 420, 920A, 920B. The clamp 1018 and tightening mechanism 1020 can secure the anchor plate 1002 to the pelvic bone 216.

Figure 11:
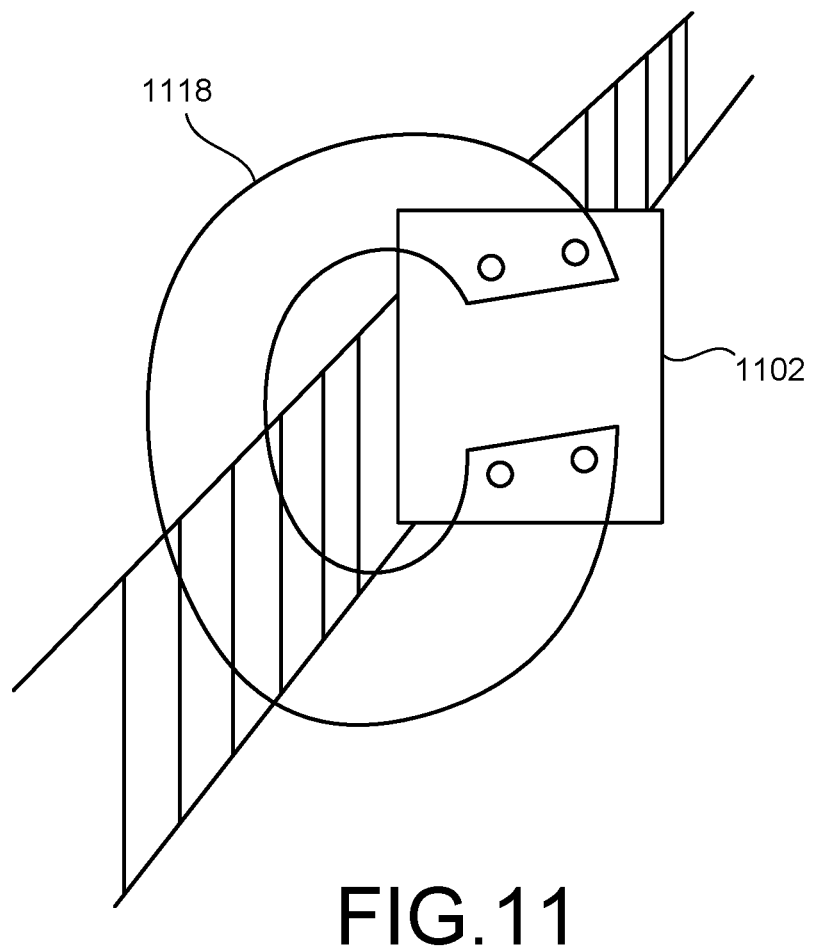
FIG. 11 illustrates a mechanism for securing an anchor plate of an implantable device to a pelvic bone.

FIG. 11 illustrates a mechanism for securing an anchor plate 1102 of an implantable device to a pelvic bone 216. In this example, the clamp 1118 is C-shaped, with two opposite end portions engaging the anchor plate 1102. The clamp 1118 can include any combination of features of the clamps 218A, 218B, 318A, 318B, 418A, 418B, 518A, 518B, 618, 918A, 918B, 1018 and/or attachment member(s) 114 described above. The anchor plate 1102 can have any combination of features of the anchor plate 102, 202, 302, 802, 902, 1002 described above. In some examples, the clamp 1118 can squeeze the pelvic bone 216 toward the anchor plate 1102, securing the anchor plate 1102 to the pelvic bone 216.

Figure 12:
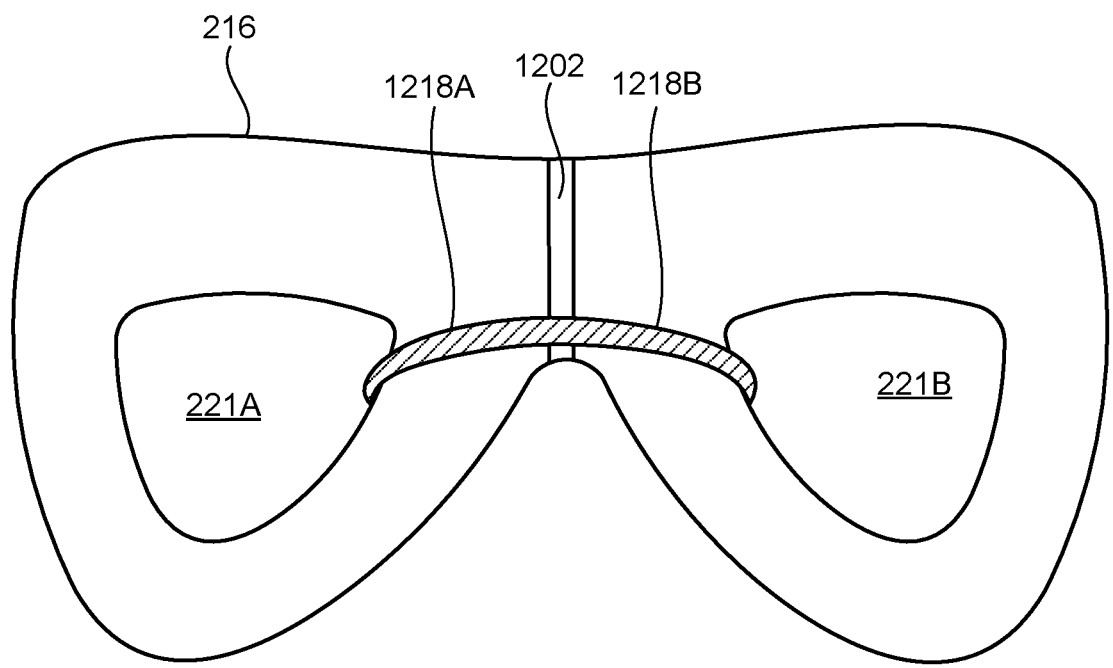
FIG. 12 illustrates a mechanism for securing an anchor plate of an implantable device to a pelvic bone.

FIG. 12 illustrates a mechanism for securing an anchor plate 1202 of an implantable device to a pelvic bone 216. In this example, the implantable device includes two clamps 1218A, 1218B that wrap around the pelvic bone 216 and extend through the obdurator foramen 221A, 221B. The clamps 1218, 1218B can secure the anchor plate 1202 to the pelvic bone 216 in a vertical direction. The clamps 1218A, 1218B can include any combination of features of the clamps 218A, 218B, 318A, 318B, 418A, 418B, 518A, 518B, 618, 918A, 918B, 1018, 1118 and/or attachment member(s) 114 described above. The anchor plate 1202 can have any combination of features of the anchor plate 102, 202, 302, 802, 902, 1002, 1102 described above.

Figure 13:
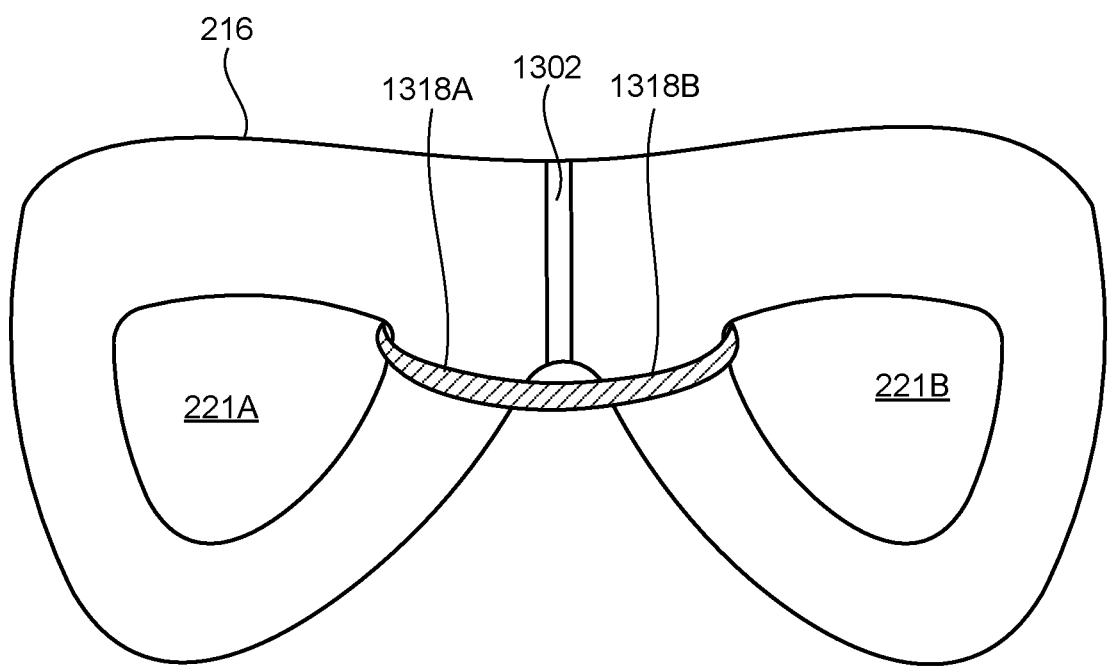
FIG. 13 illustrates a mechanism for securing an anchor plate of an implantable device to a pelvic bone.

FIG. 13 illustrates a mechanism for securing an anchor plate 1302 of an implantable device to a pelvic bone 216. In this example, the implantable device includes two clamps 1318A, 1318B that wrap around the pelvic bone 216 and extend through the obdurator foramen 221A, 221B. The clamps 1318, 1318B can secure the anchor plate 1302 to the pelvic bone 216. The clamps 1318A, 1318B can include any combination of features of the clamps 218A, 218B, 318A, 318B, 418A, 418B, 518A, 518B, 618, 918A, 918B, 1018, 1118, 1218A, 1218B and/or attachment member(s) 114 described above. The anchor plate 1302 can have any combination of features of the anchor plate 102, 202, 302, 802, 902, 1002, 1102, 1202 described above.

Figure 14:
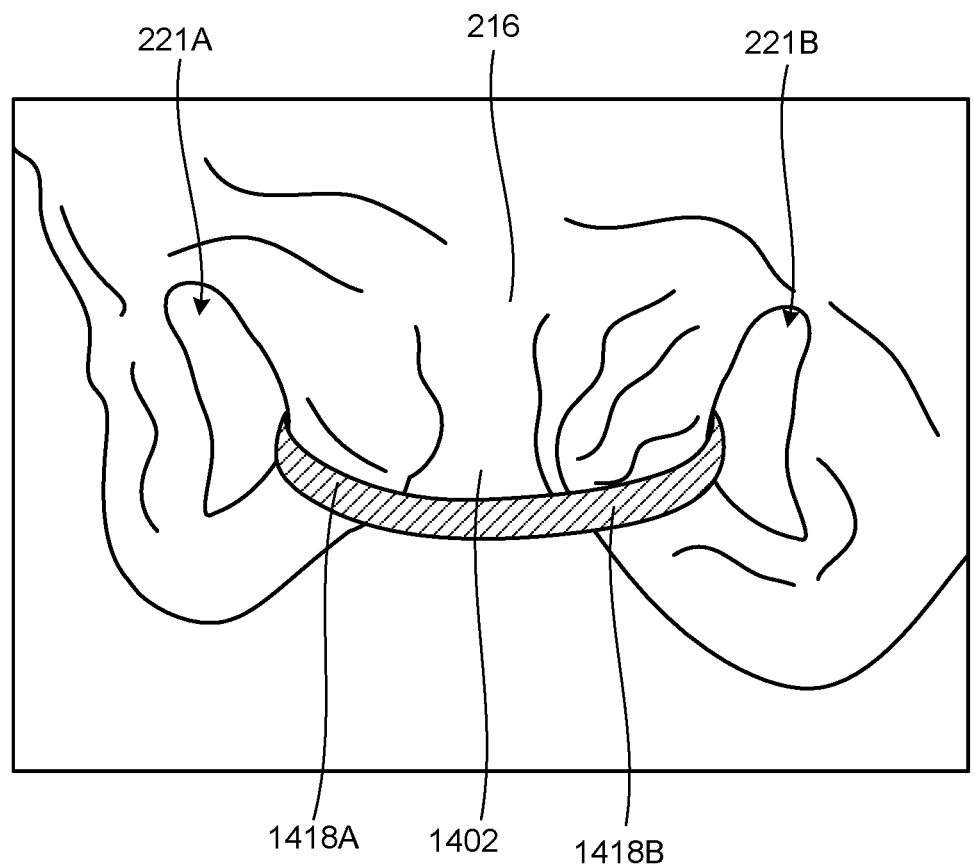
FIG. 14 illustrates a mechanism for securing an anchor plate of an implantable device to a pelvic bone.

FIG. 14 illustrates a mechanism for securing an anchor plate 1402 of an implantable device to a pelvic bone 216. In this example, the implantable device includes two clamps 1418A, 1418B that wrap around the pelvic bone 216 and extend through the obdurator foramen 221A, 221B. The clamps 1418A, 1418B can secure the anchor plate 1402 to the pelvic bone 216. The clamps 1418A, 1418B can include any combination of features of the clamps 218A, 218B, 318A, 318B, 418A, 418B, 518A, 518B, 618, 918A, 918B, 1018, 1118, 1218A, 1218B, 1318A, 1318B and/or attachment member(s) 114 described above. The anchor plate 1402 can have any combination of features of the anchor plate 102, 202, 302, 802, 902, 1002, 1102, 1202, 1302 described above.

Figure 15A:
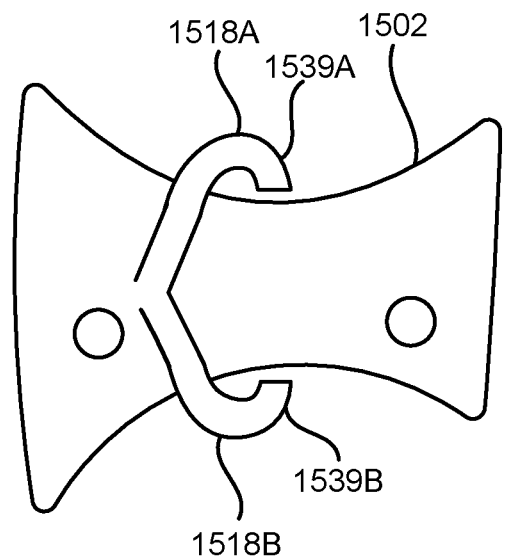
FIG. 15A illustrates a mechanism for securing an anchor plate of an implantable device to a pelvic bone.
Figure 15B:
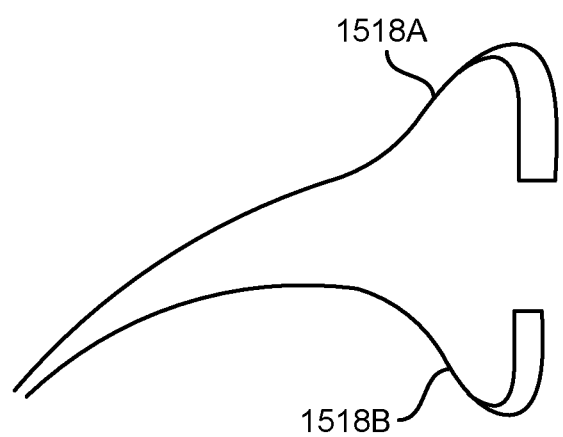
FIG. 15B illustrates a clamp used in the mechanism of FIG. 15A.

FIG. 15A illustrates a mechanism for securing an anchor plate 1502 of an implantable device to a pelvic bone, and FIG. 15B illustrates a clamp 1518A, 1518B used in the mechanism of FIG. 15A. The clamp 1518A, 1518B can include a single clamp, or two clamps working together. End portions 1539A, 1539B of the clamp(s) 1518A, 1518B can engage a side of the pelvic bone opposite from a side of the pelvic bone engaged by the anchor plate 1502, securing the anchor plate 1502 to the pelvic bone. The clamps 1518A, 1518B can include any combination of features of the clamps 218A, 218B, 318A, 318B, 418A, 418B, 518A, 518B, 618, 918A, 918B, 1018, 1118, 1218A, 1218B, 1318A, 1318B, 1418A, 1418B and/or attachment member(s) 114 described above. The anchor plate 1502 can have any combination of features of the anchor plate 102, 202, 302, 802, 902, 1002, 1102, 1202, 1302, 1402 described above.

Figure 16:
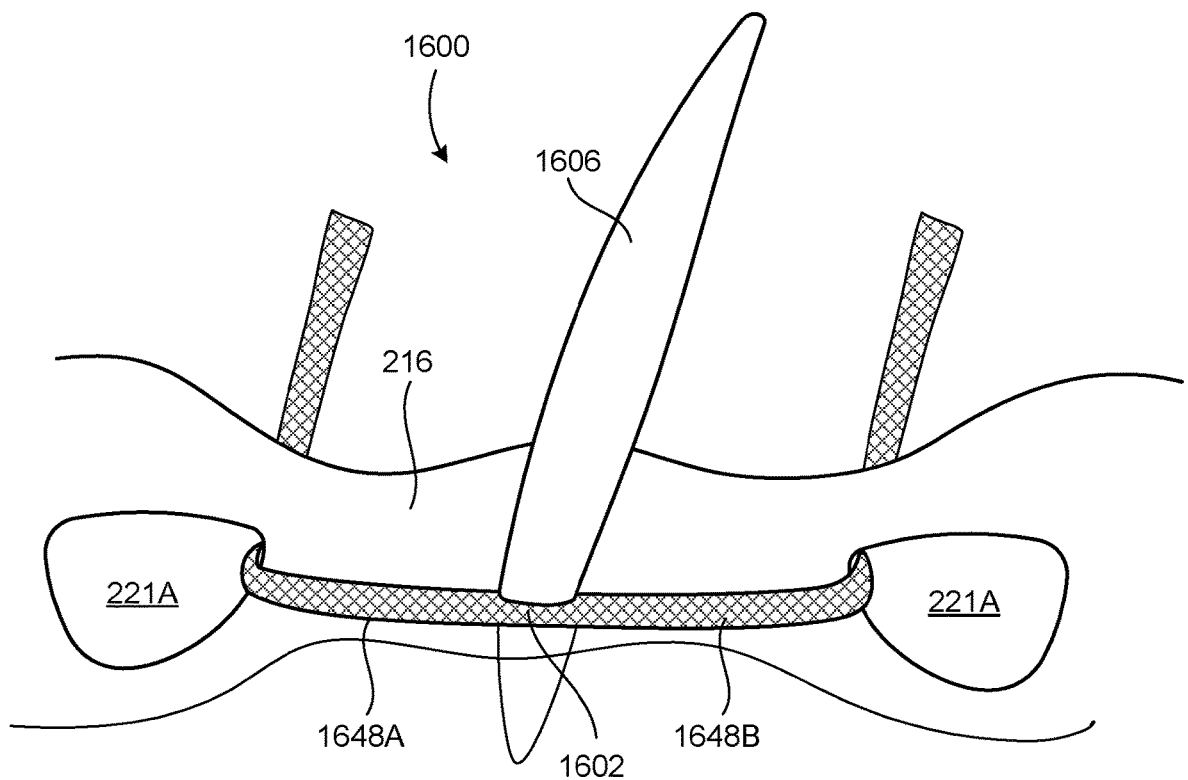
FIG. 16 illustrates an implantable device for penile construction including at least one strap for securing an anchor plate to a pelvic bone.

FIG. 16 illustrates an implantable device 1600 for penile construction including at least one strap 1648A, 1648B for securing an anchor plate 1602 to a pelvic bone 216. The straps 1648A, 1648B can be an example of the at least one attachment member 114 described above. The straps 1648A, 1648B can be attached to the anchor plate 1602 by at least one securement interface (not labeled in FIG. 16) and/or two securement interfaces, such as apertures and/or slots for the straps 1648A, 1648B to extend through. The anchor plate 1602 can have any combination of features of the anchor plate 102, 202, 302, 802, 902, 1002, 1102, 1202, 1302, 1402, 1502 described above. A penile prosthesis 1606 can extend from the anchor plate 1602. The penile prosthesis 1606 can have any combination of features of the penile prosthesis 706, 806 and/or elongated member 106 described above.

In some examples, the straps 1648A, 1648B can extend from the anchor plate 1602, through the obdurator foramen 221A, 221B. In some examples, the straps 1648A, 1648B can initially be held in place and/or secure the anchor plate in place with respect to the pelvic bone 216 by friction against soft tissue surrounding the pelvic bone 216. Tissue ingrowth can further secure the straps 1648A, 1648B against the pubic bone 216. In some examples, the straps 1648A, 1648B can include barbs and/or hooks to further secure the straps 1648A, 1648B against the pelvic bone 216. In some examples, a practitioner can suture the straps 1648A, 1648B to tissue surrounding the pelvic bone 216, such as periosteum.

In some examples, the straps 1648A, 1648B can be secured to each other on an opposite side of the pelvic bone 216 from the anchor plate 1602. In some examples, the straps 1648A, 1648B can include two separate straps individually attached to the anchor plate 1602 that can be attached to each other by a knot or self-adhesive strips, such as hook-and-loop mechanisms. In some examples, the straps 1648A, 1648B can include a single continuous strap that extends through the anchor plate 1602. In some examples, a strap(s) 1648A, 1648B that is attached to the anchor plate 1602 can be re-attached to the anchor plate 1602, enabling the practitioner to tighten the implantable device 1600 around the pelvic bone 216, such as in a zip-tie fashion.

End portions of separate straps, or first and second portions of a single strap, can engage and/or attach to each other on the opposite side of the pelvic bone 216 from the anchor plate 1602. In some examples, the end portions and/or first and second portions of the strap(s) 1648A, 1648B can attach to each other by a hook-and-loop mechanism. In some examples, the end portions and/or first and second portions of the strap(s) 1648A, 1648B can attach to each other by a buckle mechanism. In some examples, the end portions and/or first and second portions of the strap(s) 1648A, 1648B can attach to each other and/or to the pelvic bone 216 by an adhesive and/or bone cement. In some examples, the end portions and/or first and second portions of the strap(s) 1648A, 1648B can attach to each other by a zipper mechanism and/or locking eyelets with teeth. In some examples, the end portions and/or first and second portions of the strap(s) 1648A, 1648B can attach to each other by barbs. In some examples, the end portions and/or first and second portions of the strap(s) 1648A, 1648B can attach to each other and/or to the pelvic bone 216 by bone screws. In some examples, the first and second portions of the strap(s) 1648A, 1648B can define at least one, and/or multiple, strap apertures for receiving bone screws. In some examples, the strap(s) 1648A, 1648B can be secured to the pelvic bone 221 by anchor implants through and/or around the obdurator foramen 221A, 221B. In some examples, the straps 1648A, 1648B can have a mesh structure that facilitates attachment to the other strap 1648A, 1648B and/or to the pelvic bone 216. In some examples, the practitioner can attach the strap(s) 1648A, 1648B directly to the patient's soft tissue surrounding the pelvis 216. The practitioner can attach the strap(s) 1648A, 1648B directly to the patient's soft tissue by, for example, barbs or hooks in an example in which the strap(s) 1648A, 1648B includes one or more barbs and/or hooks, or by suturing the strap(s) 1648A, 1648B to tissue surrounding the pelvic bone 216.

Figure 17:
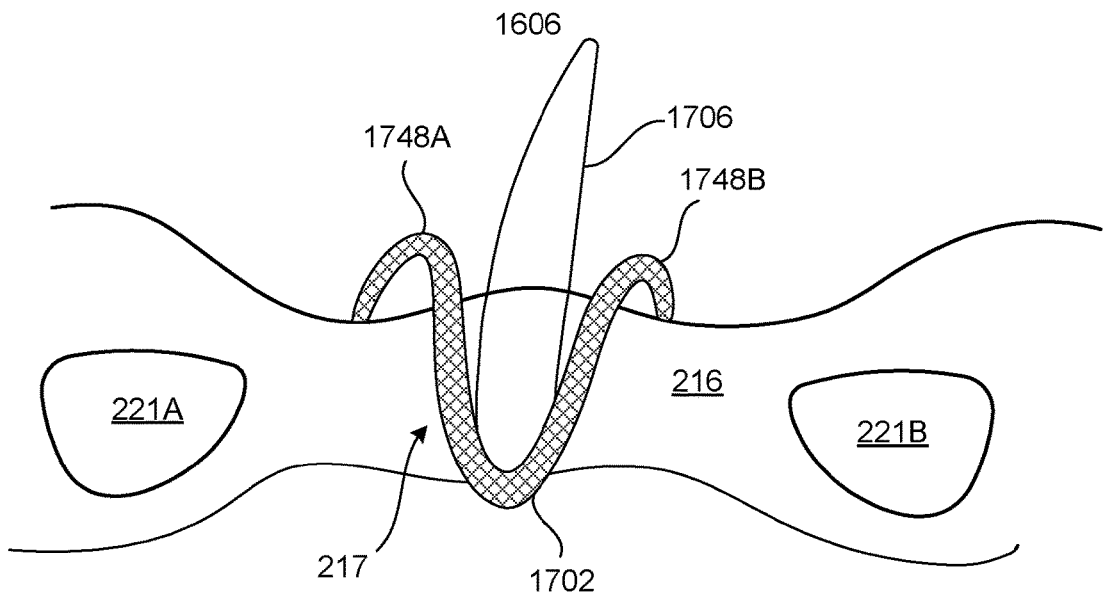
FIG. 17 illustrates an implantable device for penile construction including at least one strap for securing an anchor plate to a pelvic bone.

FIG. 17 illustrates an implantable device 1700 for penile construction including at least one strap 1648A, 1648B for securing an anchor plate 1702 to a pelvic bone 216. The anchor plate 1702 can have any combination of features of the anchor plate 102, 202, 302, 802, 902, 1002, 1102, 1202, 1302, 1402, 1502, 1602 described above. A penile prosthesis 1706 can extend from the anchor plate 1702. The penile prosthesis 1706 can have any combination of features of the penile prosthesis 706, 806, 1606 and/or elongated member 106 described above. The strap(s) 1748A, 1748B can have any combination of features of the strap(s) 1648A, 1648B and/or attachment member(s) 114 described above.

In some examples, the strap(s) 1748A, 1748B can extend and/or wrap around the pubic symphysis 217 in a vertical direction instead of a horizontal direction through the obdurator foramen 221A, 221B. In some examples, the strap(s) 1748A, 1748B can extend and/or wrap around the pubic symphysis 217 in a same direction and then attach to the anchor plate 1702. In some examples, the strap(s) 1748A, 1748B can extend and/or wrap around the pubic symphysis 217 in opposite directions and attach to each other.

Figure 18:
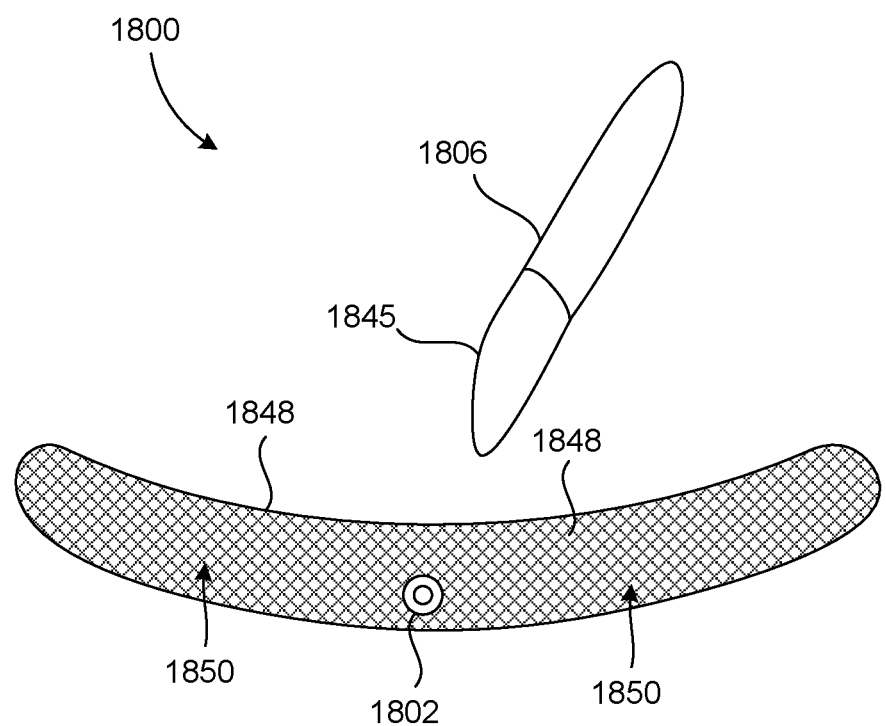
FIG. 18 illustrates an implantable device for penile construction including at least one strap for securing an anchor plate to a pelvic bone.

FIG. 18 illustrates an implantable device 1800 for penile construction including at least one strap 1848 for securing an anchor plate 1802 to a pelvic bone. The anchor plate 1802 can have any combination of features of the anchor plate 102, 202, 302, 802, 902, 1002, 1102, 1202, 1302, 1402, 1502, 1602, 1702 described above. A penile prosthesis 1806 can extend from the anchor plate 1802. A prosthesis base 1845 can be disposed at an end portion of the penile prosthesis 1806 and can engage the anchor plate 1802. The penile prosthesis 1806 can have any combination of features of the penile prosthesis 706, 806, 1606, 1706 and/or elongated member 106 described above. The strap 1848 can have any combination of features of the strap(s) 1648A, 1648B, 1748A, 1748B and/or attachment member(s) 114 described above.

In some examples, the implantable device 1800 can include a single strap 1848. The single strap 1848 can extend and/or wrap around the pelvic bone 216. A first end portion of the strap 1848 can engage a second end portion of the strap 1848, securing the strap 1848 and/or anchor plate 1802 in position with respect to the pelvic bone 216.

In some examples, the anchor plate 1802 can be woven into, and/or surrounded by, the strap 1848. The location of the anchor plate 1802 inside the strap 1848 can allow some flexibility for the anchor plate 1802 and penile prosthesis 1806, reducing the likelihood of the anchor plate 1802 or penile prosthesis 1806 being damaged during use. In some examples, the strap 1848 can have a mesh pattern 1850. The mesh pattern 1850 can increase friction between the strap 1848 and the pelvic bone 216. The increase in friction can reduce the likelihood that the strap 1848, anchor plate 1802, and/or penile prosthesis 1806 will slip and/or move with respect to the pelvic bone 216.

Figure 19A:
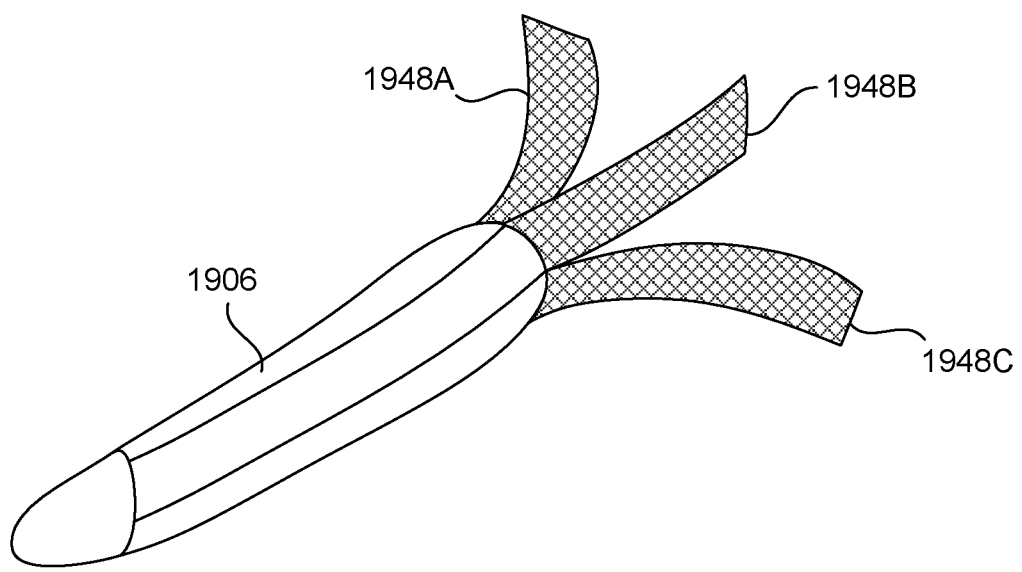
FIG. 19A illustrates a penile prosthesis and straps for attaching to a pelvic bone.

FIG. 19A illustrates a penile prosthesis 1906 and straps 1948A, 1948B, 1948C for attaching to a pelvic bone. The penile prosthesis 1906 can have any combination of features of the penile prosthesis 706, 806, 1606, 1706, 1806 and/or elongated member 106 described above. The straps 1948A, 1948B, 1948C can have any combination of features of the strap(s) 1648A, 1648B, 1748A, 1748B, 1848 and/or attachment member(s) 114 described above.

In some examples, the straps 1948A, 1948B, 1948C can surround the penile prosthesis 1906, and/or the penile prosthesis 1906 can extend through the straps 1948A, 1948B, 1948C. The straps 1948A, 1948B, 1948C can extend and/or wrap around the pelvic bone and attach to each other on an opposite side of the pelvic bone from the penile prosthesis 1906, securing the penile prosthesis 1906 to the pelvic bone.

Figure 19B:
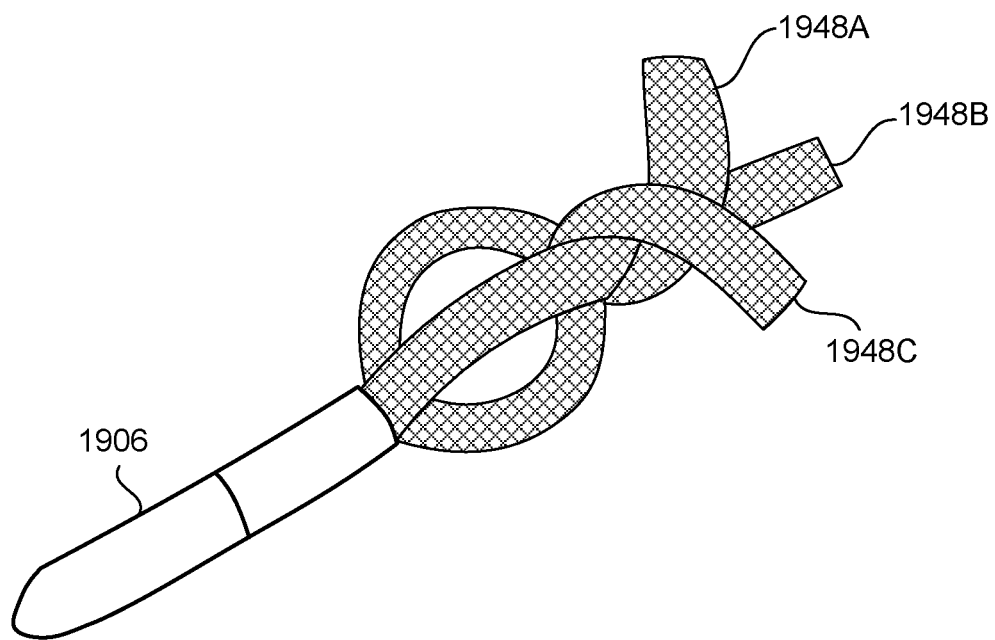
FIG. 19B illustrates the penile prosthesis and straps of FIG. 19A with the straps engaging each other.

FIG. 19B illustrates the penile prosthesis 1906 and straps 1948A, 1948B, 1948C of FIG. 19A with the straps 1948A, 1948B, 1948C engaging each other. In this example, the straps 1948A, 1948B, 1948C are engaged to each other at end portions opposite from the penile prosthesis 1906. While the pelvic bone 206 is not shown in FIG. 19B, the straps 1948A, 1948B, 1948C can be wrapped around the pelvic bone 216, as shown in FIGS. 16 and 17. When the straps 1948A, 1948B, 1948C are wrapped tightly around the pelvic bone, the penile prosthesis 1906 can be secured in place with respect to the pelvic bone.

Figure 20:
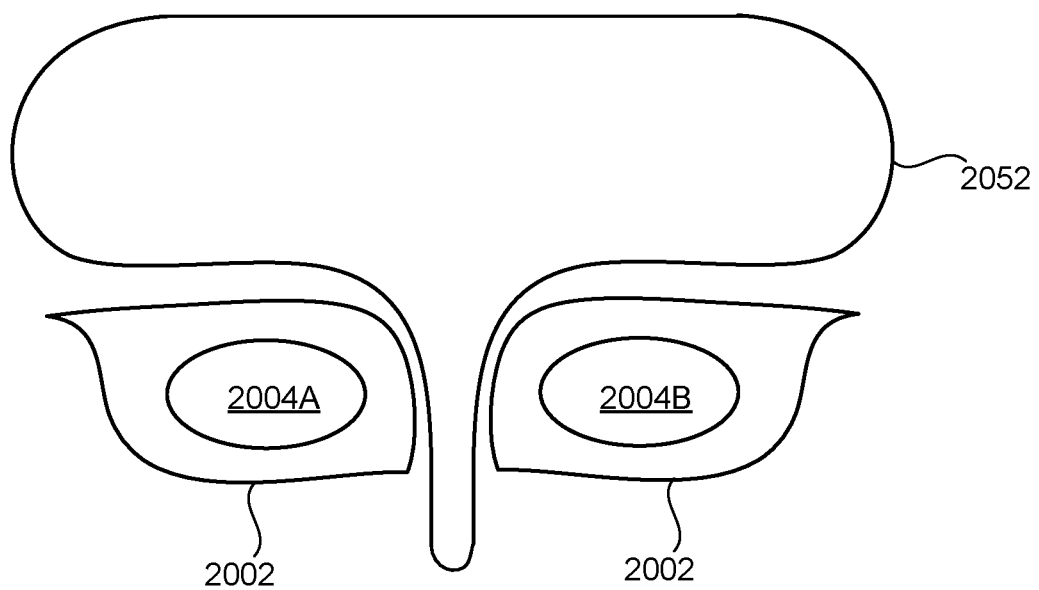
FIG. 20 illustrates a mesh for securing an anchor plate to a pelvic bone.

FIG. 20 illustrates a strap 2052 for securing an anchor plate 2002 to a pelvic bone 216 (not shown in FIG. 20). The anchor plate 2002 define two apertures. 2004A, 2004B. In some examples, the apertures 2004A, 2004B can enable snap-fit connections with elongated members, such as cylinders. In some examples, the apertures 2004A, 2004B can enable the practitioner to pull the strap 2052 through the apertures 2004A, 2004B and through the anchor plate 2002 to secure the anchor plate 2002 to the pelvic bone by tying opposite ends of the strap 2052 together. The anchor plate 2002 can have any combination of features of the anchor plate 102, 202, 302, 802, 902, 1002, 1102, 1202, 1302, 1402, 1502, 1602, 1702, 1802 described above. The strap 2052 can be an example of the attachment member 114 described above with respect to FIG. 1.

The strap 2052 can loop and/or extend around the pelvic bone in multiple configurations, such as around the pubic symphysis and/or through the obdurator foramen. The strap 2052 can have an adjustable tension to fit the pelvic bone of a particular patient. Portions of the strap 2052 can engage and/or attach to each other by a zip-tie mechanism and/or locking nuts and eyelets to secure the strap 2052, anchor plate 2002, and/or penile prosthesis in place with respect to the pelvic bone 216.

Figure 21:
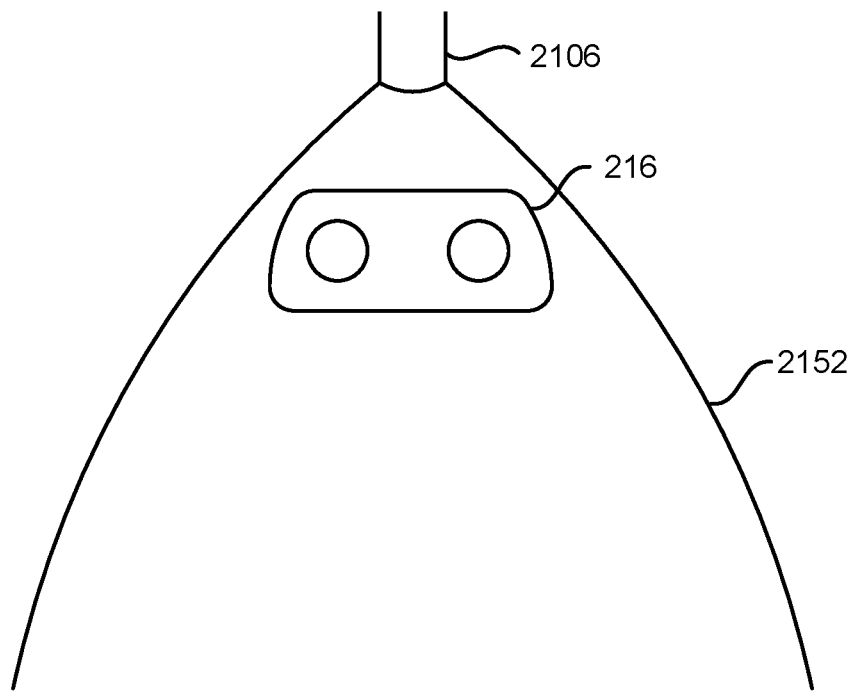
FIG. 21 illustrates a mesh for securing an anchor plate to a pelvic bone.

FIG. 21 illustrates a mesh 2152 for securing an anchor plate to a pelvic bone 216. The mesh 2152 can have any combination of features of the mesh 2052 and/or attachment member 114 described above.

Figure 22:
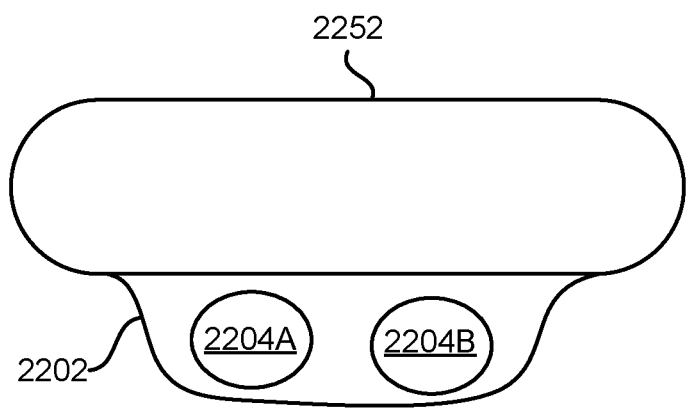
FIG. 22 illustrates a mesh for securing an anchor plate to a pelvic bone.

FIG. 22 illustrates a mesh 2252 for securing an anchor plate 2202 to a pelvic bone. The mesh 2252 can have any combination of features of the mesh 2052, 2152 and/or attachment member 114 described above. The anchor plate 2202 can define apertures 2204A, 2204B. The apertures 2204A, 2204B can enable snap-fit connections with elongated members, such as cylinders.

Figure 23:
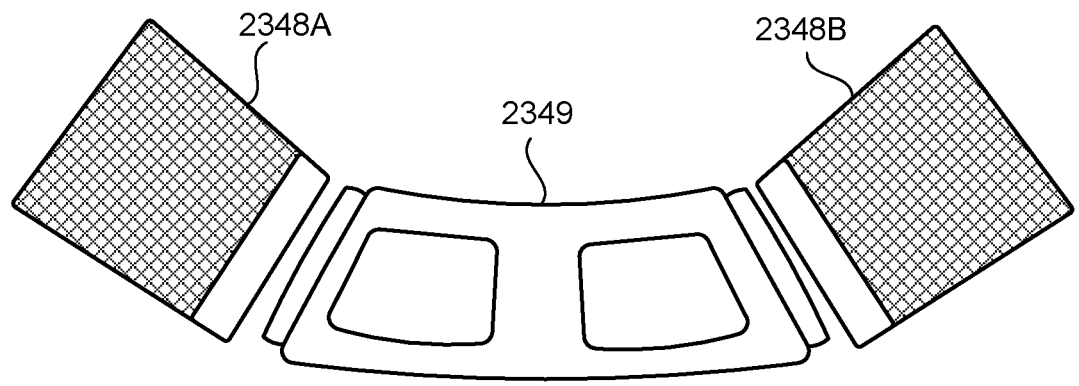
FIG. 23 shows a center piece and straps for securing the anchor plate to a pelvic bone.

FIG. 23 shows a center piece 2349 and straps 2348A, 2348B for securing the anchor plate to a pelvic bone. The center piece 2349 can be an example of the anchor plate. The straps 2348A, 2348B, which can be considered arms and/or mesh arms, can have any combination of features of the strap(s) 1648A, 1648B, 1748A, 1748B, 1848, 1948A, 1948B and/or attachment member(s) 114 described above. The straps 2348A, 2348B can engage and/or attach to the center piece 2349. The straps 2348A, 2348B can engage and/or attach to the center piece 2349 by, for example, a tongue-and-groove mating feature. The straps 2348A, 2348B and center piece 2349 can form a single strap in a one-, two-, or three-strap (or more) implantable device. The inclusion of the center piece 2349 can allow for modularity and interchangeability of the anchoring mechanism of the implantable device.

Figure 24:
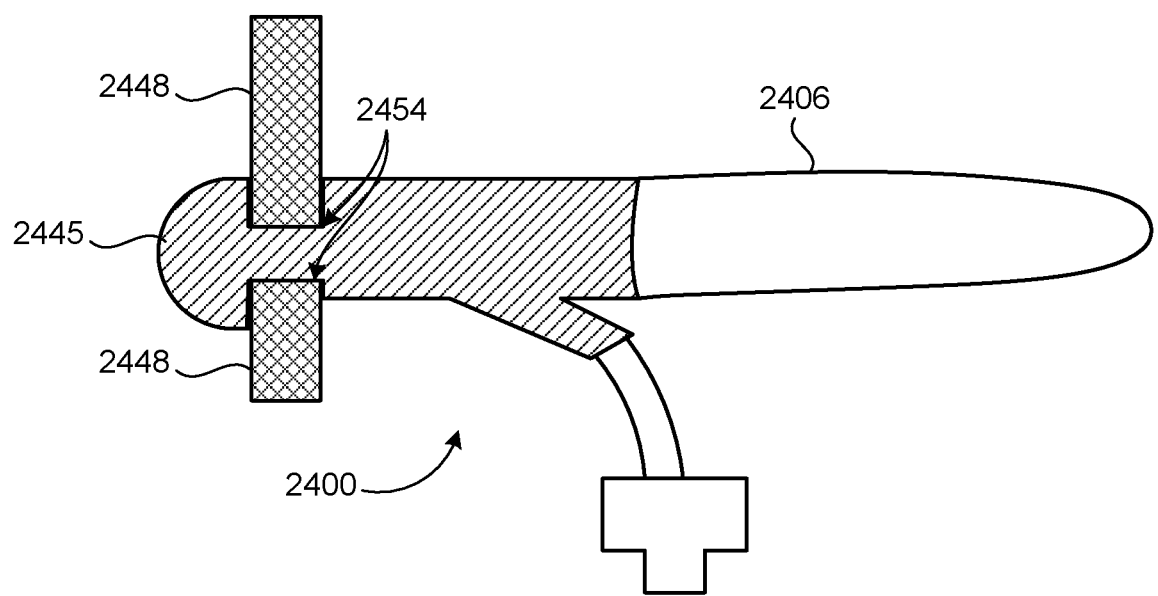
FIG. 24 illustrates an implantable device with a strap for securing an anchor plate to a pelvic bone.

FIG. 24 illustrates an implantable device 2400 with a strap 2448 for securing an anchor plate to a pelvic bone. In some examples, FIG. 24 can show a cross section of a rear-tip snap interface of the anchor plate. The strap 2448 can include any combination of features of the strap(s) 1648A, 1648B, 1748A, 1748B, 1848, 1948A, 1948B, 2348A, 2348B and/or attachment member(s) 114 described above.

In some examples, a base 2445 of the penile prosthesis 2406, and/or of the anchor plate, can define a slot 2454. The strap 2448 can extend through the slot 2454. The slot 2454 can be an example of an interface on the anchor plate for attaching the anchor plate to an attachment member 114.

Figure 25:
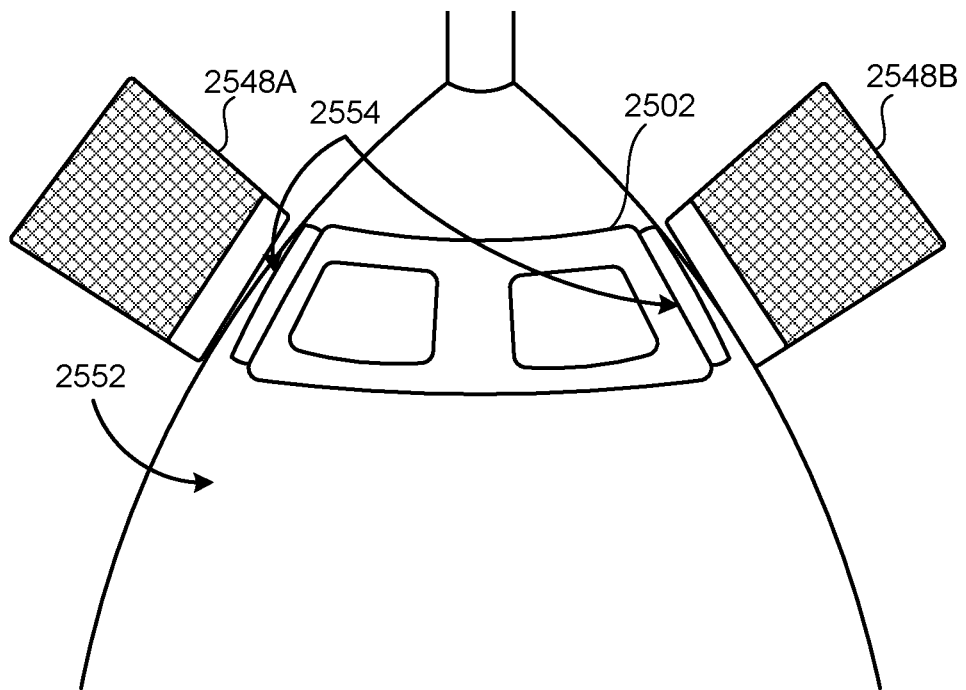
FIG. 25 illustrates an implantable device with a mesh for securing an anchor plate to a pelvic bone.

FIG. 25 illustrates an implantable device with a mesh 2552 for securing an anchor plate 2502 to a pelvic bone. The anchor plate 2502 can have any combination of features of the anchor plate 102, 202, 302, 802, 902, 1002, 1102, 1202, 1302, 1402, 1502, 1602, 1702, 1802 described above. The anchor plate 2502 can define a slot 2554 for receiving and/or securing the mesh 2552. The mesh 2552 can have any combination of features of the mesh 2052, 2152, 2252 and/or attachment member 114 described above. In some examples, a practitioner can loop and/or wrap mesh arms 2548A, 2548B, which can be attached to the mesh 2552, around the pelvic bone and tie the mesh arms 2548A, 2548B together. In some examples, the mesh arms 2548A, 2548B can include locking eyelets, such as locking eyelets with teeth, that allow the mesh arms 2548A, 2548B to move in only one direction through the slot 2554, tightening the anchor plate 2502 to the pelvic bone.

Figure 26:
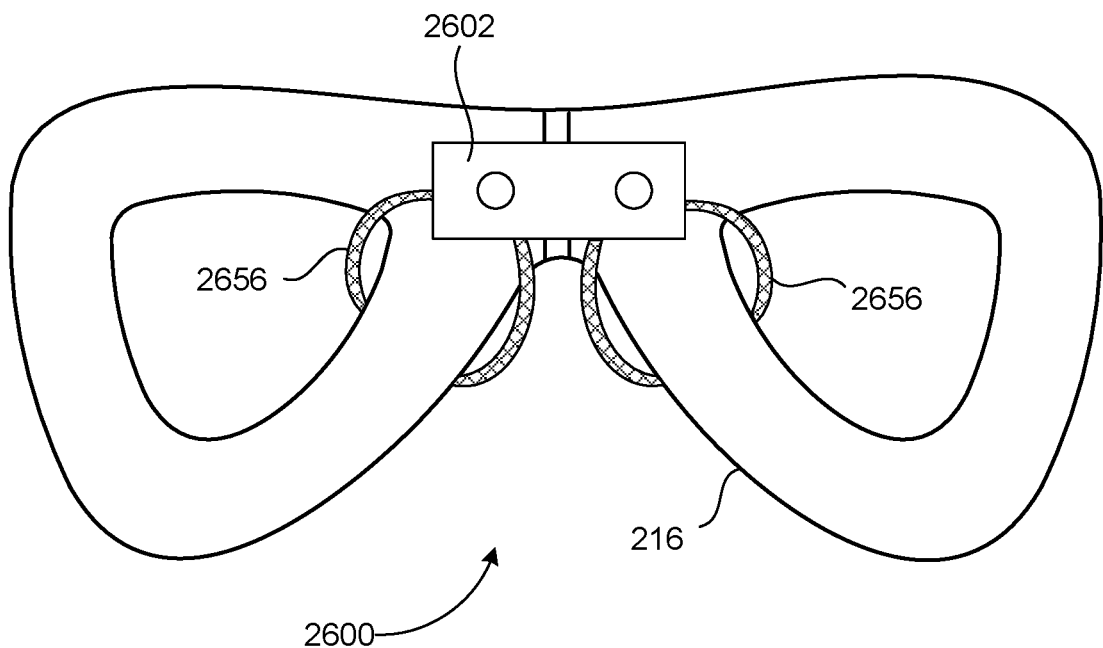
FIG. 26 illustrates an implantable device with a sling for securing an anchor plate to a pelvic bone.

FIG. 26 illustrates an implantable device 2600 with a sling 2556 for securing an anchor plate 2602 to a pelvic bone 216. The anchor plate 2602 can have any combination of features of the anchor plate 102, 202, 302, 802, 902, 1002, 1102, 1202, 1302, 1402, 1502, 1602, 1702, 1802, 2502 described above. The sling 2556 can include any combination of features of the strap(s) 1648A, 1648B, 1748A, 1748B, 1848, 1948A, 1948B, 2348A, 2348B, 2448 and/or attachment member(s) 114 described above. The sling 2556 can extend from the anchor plate 2602 around the pelvic bone 216, securing the anchor plate 2602 to the pelvic bone 216. The implantable device 2600 could include one, two, or more slings 2556. The sling 2556 can extend through one or more slots defined by the anchor plate 2602. The slot(s) can allow the anchor plate 2602 to slide with respect to the sling 2556, allowing a practitioner to adjust the location of the anchor plate 2602 and/or implantable device 2600 with respect to the pelvic bone 216. The practitioner can tighten the sling 2556 to secure the anchor plate 2602 and/or implantable device 2600 in place with respect to the pelvic bone 216.

In the following some examples will be described.

Example 1: An implantable device for penile construction can comprise an anchor plate and at least one attachment member. The anchor plate can be to engage with a first portion of a pelvic bone of a patient. The anchor plate can comprise a prosthesis attachment interface configured to be coupled to a penile prosthesis. The at least one attachment member can be configured to attach to the anchor plate. The at least one attachment member can be configured to engage with a second portion of the pelvic bone of the patient. The engagement of the anchor plate with the first portion of the pelvic bone and the engagement of the attachment member with the second portion of the pelvic bone can couple the pelvic bone between the anchor plate and the at least one attachment member.

Example 2: The implantable device of example 1, wherein the prosthesis attachment interface comprises an elastic material configured to attach to the anchor plate and to the penile prosthesis.

Example 3: The implantable device of either of examples 1 or 2, wherein the prosthesis attachment interface defines a prosthesis anchor aperture, and the implantable device further comprises a threaded fastener. The threaded fastener can be configured to extend through a prosthesis attachment aperture defined by the penile prosthesis and into the prosthesis anchor aperture.

Example 4: The implantable device of any of examples 1-3, wherein the attachment member comprises at least one clamp.

Example 5: The implantable device of example 4, wherein the at least one clamp defines a clamp aperture with threads, and the implantable device further comprises a set screw. The set screw can be configured to extend through the clamp aperture and reduce a distance between the anchor plate and an end portion of the clamp opposite from the aperture.

Example 6: The implantable device of example 4, wherein the at least one clamp comprises a first end portion configured to attach to the anchor plate and a second end portion configured to engage the pelvic bone, and the implantable device further comprises a tightening mechanism. The tightening mechanism can be configured to increase a distance between the anchor plate and the second end portion of the clamp.

Example 7: The implantable device of example 4, wherein the at least one clamp comprises a first clamp and a second clamp, the first clamp comprising a first end portion configured to attach to the anchor plate and a second end portion configured to engage the pelvic bone, the second clamp comprising a first end portion to attach to the anchor plate and a second end portion configured to engage the pelvic bone, the implantable device further comprises at least one tightening mechanism. The at least one tightening mechanism can be configured to reduce a distance between the second end portion of the first clamp and the anchor plate independently of a distance between the second end portion of the second clamp and the anchor plate, and reduce the distance between the second end portion of the second clamp and the anchor plate independently of the distance between the second end portion of the first clamp and the anchor plate.

Example 8: The implantable device of any of examples 4-7, wherein the tightening mechanism comprises at least one release button, the at least one release button being configured to allow the distance between at least one of the second end portion of the clamp and the anchor plate, the second end portion of the first clamp and the anchor plate, or the second end portion of the second clamp and the anchor plate, to increase.

Example 9: The implantable device of example 4, further comprising a leaf spring. The leaf spring can comprise a first clamp, a second clamp, and a nut. The nut can define nut threads. The first clamp and the second clamp can comprise clamp threads configured to receive the nut threads.

Example 10: The implantable device of any of examples 1-3, wherein the at least one attachment member comprises a strap.

Example 11: The implantable device of example 10, wherein the strap comprises a mesh pattern.

Example 12: The implantable device of either of examples 10 or 11, wherein the anchor plate comprises a first securement interface and a second securement interface, and the strap comprises a first portion configured to engage the first securement interface and a second portion configured to engage the second securement interface.

Example 13: The implantable device of either of examples 10 or 11, wherein the anchor plate comprises at least one securement interface, the strap is configured to engage the at least one securement interface, and a first portion of the strap is configured to engage a second portion of the strap.

Example 14: The implantable device of example 13, wherein the first portion of the strap is configured to engage the second portion of the strap by at least one of, a hook-and-loop mechanism, a buckle mechanism, an adhesive, or a zipper mechanism.

Example 15: The implantable device of example 14, wherein the anchor plate comprises at least one securement interface, the strap is configured to engage the at least one securement interface, and the strap defines at least one strap aperture configured to receive a bone screw, the bone screw securing the strap to the pelvic bone.

Example 16: An implantable device for penile construction can comprise an anchor plate and at least one clamp. The anchor plate can be configured to engage with a first portion of a pelvic bone of a patient. The anchor plate can comprise a prosthesis attachment interface configured to be coupled to a penile prosthesis. The prosthesis attachment interface can comprise an elastic material. The least one clamp can be rotatably attached to the anchor plate. The at least one clamp can be configured to engage with a second portion of the pelvic bone of the patient. The engagement of the anchor plate with the first portion of the pelvic bone and the engagement of the at least one clamp with the second portion of the pelvic bone can friction-fit the pelvic bone between the anchor plate and the at least one clamp.

Example 17: The implantable device of example 16, wherein the at least one clamp comprises a first end portion configured to attach to the anchor plate and a second end portion configured to engage the pelvic bone, and the implantable device further comprises a tightening mechanism, the tightening mechanism being configured to increase a distance between the anchor plate and the second end portion of the clamp.

Example 18: The implantable device of example 16, wherein the at least one clamp comprises a first clamp and a second clamp, the first clamp comprising a first end portion configured to attach to the anchor plate and a second end portion configured to engage the pelvic bone, the second clamp comprising a first end portion configured to attach to the anchor plate and a second end portion configured to engage the pelvic bone, and the implantable device further comprises at least one tightening mechanism. The at least one tightening mechanism can be configured to reduce a distance between the second end portion of the first clamp and the anchor plate independently of a distance between the second end portion of the second clamp and the anchor plate, and reduce the distance between the second end portion of the second clamp and the anchor plate independently of the distance between the second end portion of the first clamp and the anchor plate.

Example 19: An implantable device for penile construction can comprise an anchor plate and at least one strap. The anchor plate can be configured to engage with a first portion of a pelvic bone of a patient. The anchor plate can comprise a prosthesis attachment interface configured to be coupled to a penile prosthesis. The prosthesis attachment interface can comprise an elastic material. The at least one strap can be attached to the anchor plate. The at least one strap can be configured to engage with a second portion of the pelvic bone of the patient. The engagement of the anchor plate with the first portion of the pelvic bone and the engagement of the at least one strap with the second portion of the pelvic bone can friction-fit the pelvic bone between the anchor plate and the at least one strap.

Example 20: The implantable device of example 19, wherein the anchor plate comprises at least one securement interface, the strap is configured to engage the at least one securement interface, and a first portion of the strap is configured to engage a second portion of the strap.

While certain features of the described implementations have been illustrated as described herein, many modifications, substitutions, changes and equivalents will now occur to those skilled in the art. It is, therefore, to be understood that the appended claims are intended to cover all such modifications and changes as fall within the true spirit of the embodiments of the invention.

What is claimed is:

1. An implantable device for penile construction, the implantable device comprising:
   an anchor plate configured to engage with a first portion of a pelvic bone of a patient, the anchor plate comprising a prosthesis attachment interface configured to be coupled to a penile prosthesis;
   at least one attachment member configured to attach to the anchor plate, the at least one attachment member being configured to engage with a second portion of the pelvic bone of the patient, the engagement of the anchor plate with the first portion of the pelvic bone and the engagement of the attachment member with the second portion of the pelvic bone coupling the pelvic bone between the anchor plate and the at least one attachment member, the attachment member includes a clamp, the clamp having a first end portion configured to attach to the anchor plate and a second end portion configured to engage the pelvic bone; and
   a tightening mechanism configured to change a distance between the anchor plate and the second end portion of the clamp.

2. The implantable device of claim 1, wherein the prosthesis attachment interface comprises an elastic material configured to attach to the anchor plate and to the penile prosthesis.

3. The implantable device of claim 1, wherein:
   the prosthesis attachment interface defines a prosthesis anchor aperture; and
   the implantable device further comprises a threaded fastener, the threaded fastener being configured to extend through the anchor aperture and into a prosthesis attachment aperture defined by the penile prosthesis and into the prosthesis anchor aperture.

4. The implantable device of claim 1, wherein the tightening mechanism includes a release button, the release button being configured to allow the distance between the second end portion of the clamp and the anchor plate to increase.

5. An implantable device for penile construction, the implantable device comprising:
   an anchor plate configured to engage with a first portion of a pelvic bone of a patient, the anchor plate comprising a prosthesis attachment interface configured to be coupled to a penile prosthesis, the prosthesis attachment interface comprising an elastic material; and
   at least one clamp rotatably attached to the anchor plate, the at least one clamp being configured to engage with a second portion of the pelvic bone of the patient, the engagement of the anchor plate with the first portion of the pelvic bone and the engagement of the at least one clamp with the second portion of the pelvic bone friction-fitting the pelvic bone between the anchor plate and the at least one clamp.

6. The implantable device of claim 5, wherein:
   the at least one clamp comprises a first end portion configured to attach to the anchor plate and a second end portion configured to engage the pelvic bone; and
   the implantable device further comprises a tightening mechanism, the tightening mechanism being configured to increase a distance between the anchor plate and the second end portion of the clamp.

7. The implantable device of claim 5, wherein:
   the at least one clamp comprises a first clamp and a second clamp, the first clamp comprising a first end portion configured to attach to the anchor plate and a second end portion configured to engage the pelvic bone, the second clamp comprising a first end portion configured to attach to the anchor plate and a second end portion configured to engage the pelvic bone; and
   the implantable device further comprises at least one tightening mechanism, the at least one tightening mechanism being configured to:
      reduce a distance between the second end portion of the first clamp and the anchor plate independently of a distance between the second end portion of the second clamp and the anchor plate; and
      reduce the distance between the second end portion of the second clamp and the anchor plate independently of the distance between the second end portion of the first clamp and the anchor plate.

8. An implantable device for penile construction, the implantable device comprising:
   an anchor plate configured to engage with a first portion of a pelvic bone of a patient, the anchor plate comprising a prosthesis attachment interface configured to be coupled to a penile prosthesis;

at least one attachment member configured to attach to the anchor plate, the at least one attachment member being configured to engage with a second portion of the pelvic bone of the patient, the engagement of the anchor plate with the first portion of the pelvic bone and the engagement of the attachment member with the second portion of the pelvic bone coupling the pelvic bone between the anchor plate and the at least one attachment member, the attachment member includes a first clamp and a second clamp, the first clamp having a first end portion configured to attach to the anchor plate and a second end portion configured to engage the pelvic bone, the second clamp having a first end portion to attach to the anchor plate and a second end portion configured to engage the pelvic bone; and a tightening mechanism, the tightening mechanism being configured to:

reduce a distance between the second end portion of the first clamp and the anchor plate independently of a distance between the second end portion of the second clamp and the anchor plate; and reduce the distance between the second end portion of the second clamp and the anchor plate independently of the distance between the second end portion of the first clamp and the anchor plate.

9. The implantable device of claim 8, wherein the tightening mechanism includes at least one release button, the at least one release button being configured to allow the distance between the second end portion of the first clamp and the anchor plate to increase.

10. The implantable device of claim 8, wherein the prosthesis attachment interface includes an elastic material configured to attach to the anchor plate and to the penile prosthesis.

* * * * *